(12) United States Patent
Genosar

(10) Patent No.: US 10,716,901 B2
(45) Date of Patent: Jul. 21, 2020

(54) AUTO-INJECTOR

(71) Applicant: Aktivax, Inc., Broomfield, CO (US)

(72) Inventor: Amir Genosar, Boulder, CO (US)

(73) Assignee: AKTIVAX, Inc., Broomfield, CO (US)

( * ) Notice: Subject to any disclaimer, the term of this patent is extended or adjusted under 35 U.S.C. 154(b) by 294 days.

(21) Appl. No.: 15/517,129

(22) PCT Filed: Dec. 5, 2015

(86) PCT No.: PCT/US2015/064145
§ 371 (c)(1),
(2) Date: Apr. 5, 2017

(87) PCT Pub. No.: WO2016/058009
PCT Pub. Date: Apr. 14, 2016

(65) Prior Publication Data
US 2017/0246393 A1    Aug. 31, 2017

Related U.S. Application Data

(60) Provisional application No. 62/060,079, filed on Oct. 6, 2014.

(51) Int. Cl.
| | |
|---|---|
| *A61M 5/20* | (2006.01) |
| *A61M 5/32* | (2006.01) |
| *A61M 5/00* | (2006.01) |
| *A61M 39/22* | (2006.01) |
| *A61M 5/28* | (2006.01) |
| *A61M 5/31* | (2006.01) |

(52) U.S. Cl.
CPC .......... *A61M 5/2066* (2013.01); *A61M 5/008* (2013.01); *A61M 5/2053* (2013.01); *A61M 5/3234* (2013.01); *A61M 39/22* (2013.01); *A61M 5/282* (2013.01); *A61M 2005/206* (2013.01); *A61M 2005/2026* (2013.01); *A61M 2005/3126* (2013.01); *A61M 2209/088* (2013.01)

(58) Field of Classification Search
CPC .. A61M 5/2066; A61M 39/22; A61M 5/3234; A61M 5/008; A61M 5/2053; A61M 2209/088; A61M 2005/2026; A61M 2005/3126; A61M 2005/206; A61M 5/282
See application file for complete search history.

(56) References Cited

U.S. PATENT DOCUMENTS

| | | |
|---|---|---|
| 5,616,135 A | 4/1997 | Thorne |
| 6,149,626 A | 11/2000 | Bachynsky et al. |

(Continued)

OTHER PUBLICATIONS

European patent Application No. 15848778.5, Extended European Search Report dated May 15, 2018, 8 pages.

(Continued)

*Primary Examiner* — Amber R Stiles
(74) *Attorney, Agent, or Firm* — Holzer Patel Drennan

(57) ABSTRACT

An auto-injector operable in a single activation step. The auto-injector is automatically armed when removed from its carrying receptacle. The auto-injector may be prefilled with more than one constituent of a beneficial agent, stored in separated compartments, in such an arrangement that the compartments will automatically merge when the auto-injector is removed from its carrying receptacle.

12 Claims, 23 Drawing Sheets

(56) References Cited

U.S. PATENT DOCUMENTS

| | | | |
|---|---|---|---|
| 2003/0171717 A1* | 9/2003 | Farrugia | A61M 5/2033 604/131 |
| 2004/0249339 A1* | 12/2004 | Willis | A61M 5/30 604/70 |
| 2005/0171477 A1 | 8/2005 | Rubin et al. | |
| 2010/0016795 A1 | 1/2010 | McLoughlin | |
| 2010/0185148 A1* | 7/2010 | Gillespie, III | A61M 5/2033 604/110 |
| 2011/0046565 A1* | 2/2011 | Radmer | A61M 5/20 604/211 |
| 2012/0172804 A1 | 7/2012 | Plumptre | |
| 2013/0184649 A1 | 7/2013 | Edwards et al. | |

OTHER PUBLICATIONS

PCT/US2015/064145, International Search Report and Written Opinion, dated Apr. 1, 2016, 11 pages.

\* cited by examiner

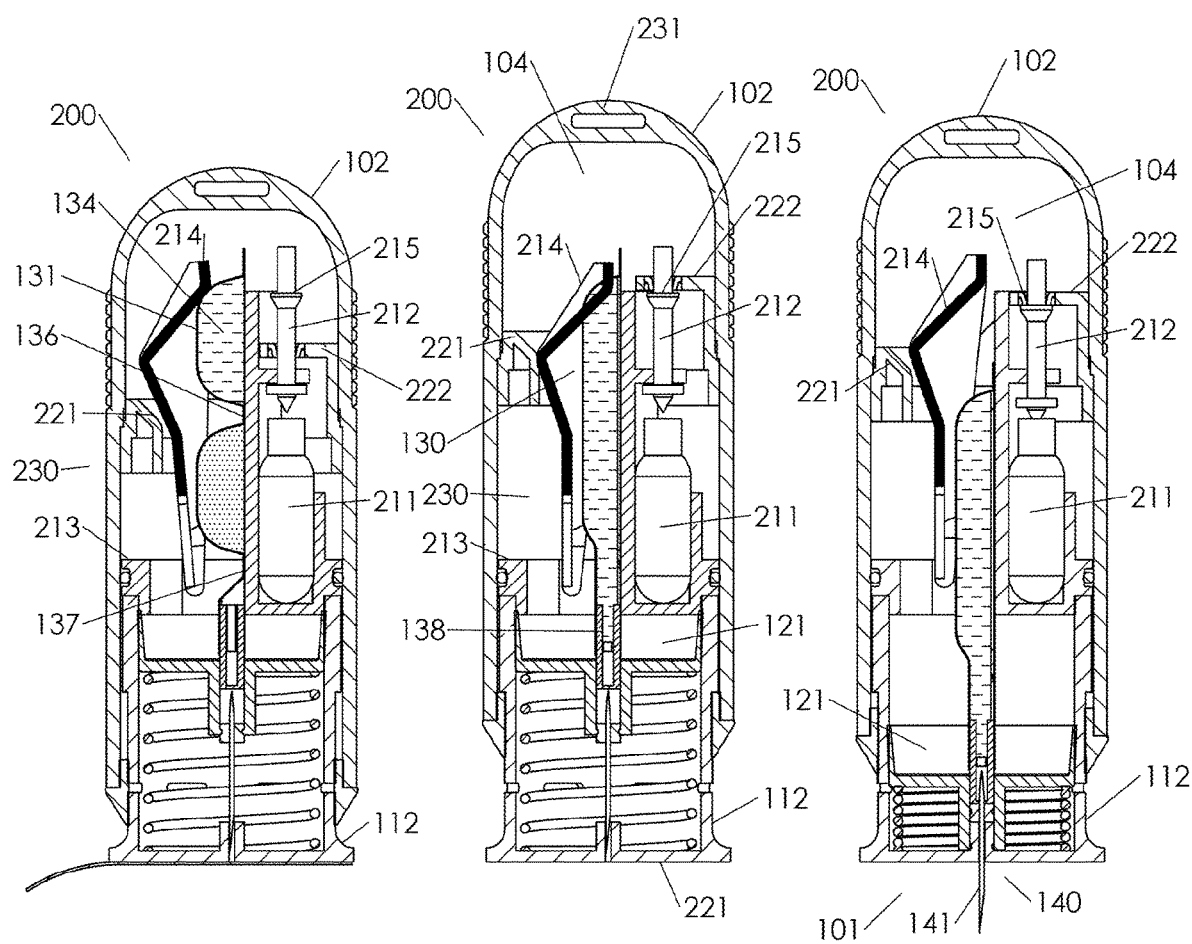

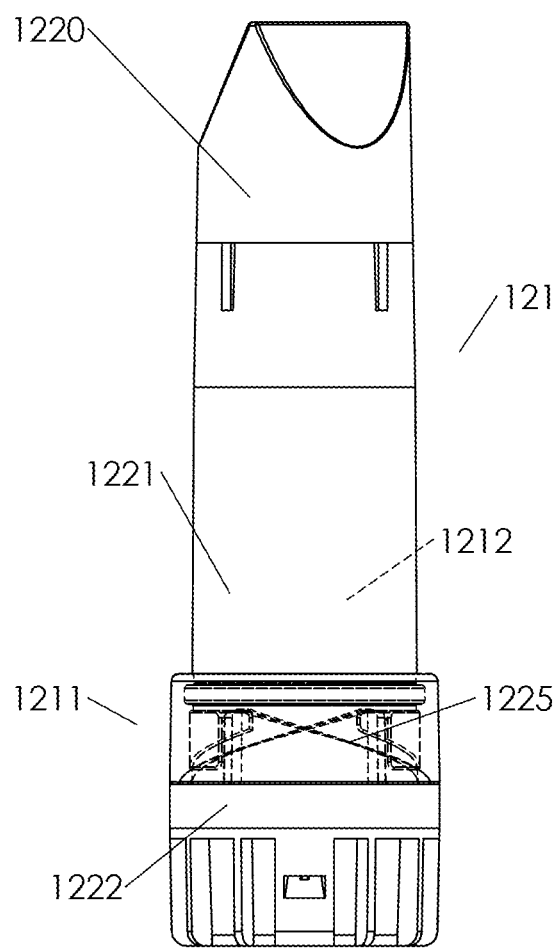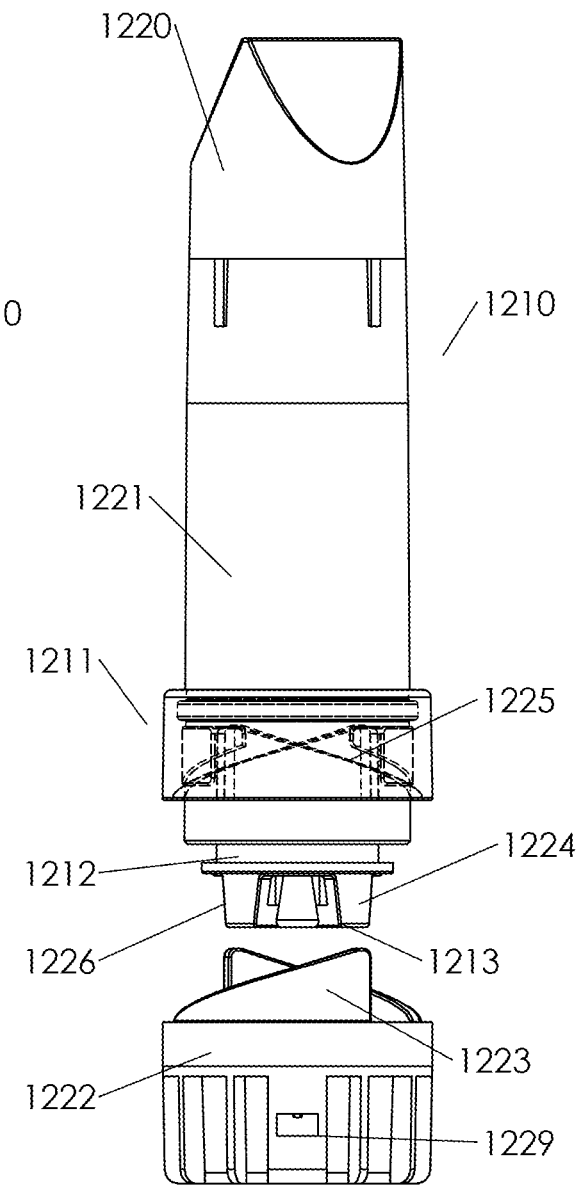
Figure 12a                          Figure 12b

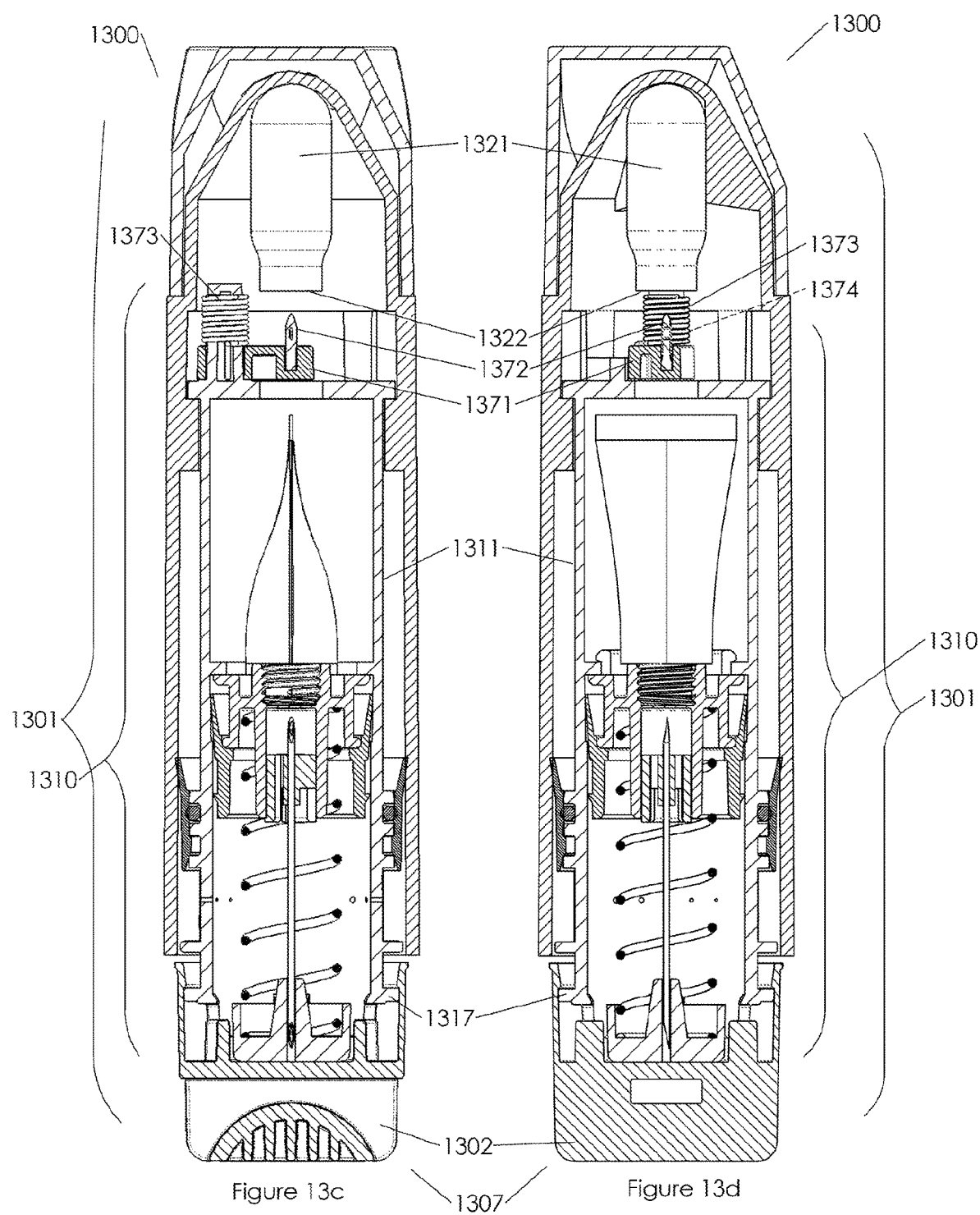

AUTO-INJECTOR

FIELD

The present disclosure pertains to the field of parenteral drug delivery, and more particularly to prefilled injection devices.

BACKGROUND

Auto-injectors are used for clinical parenteral administration of a fixed dose of a beneficial agent to a subject. They are particularly advantageous, and hence more commonly practiced, in emergency applications in which proper administration, potentially by an untrained or minimally trained user, under extreme duress, in less than optimal conditions, is needed to be perform in a timely manner. Auto-injectors are more proper for these applications than regular syringes as they require fewer and simpler to implement operative steps. It is hence an important aspect of auto-injector design to minimize the number and complexity of the operation steps of an auto-injector. Many auto-injector technologies require two hand preparation of the device for injection, such as arming of the device, release of a safety catch, and removal of an aseptic barrier that ensure the sterility of the device until the time of use. According to one usability aspect of auto-injectors, the need to perform two hand operations introduces a level of complexity and confusion to the user, as eventually the device has to be properly repositioned, in the proper orientation, in the hand that is used for administration.

One example of an commonly used auto-injector is the EpiPen® manufactured by Meridain Medical Technologies (Columbia, Md.). The EpiPen® applies a spring force to automatically deliver a dose of epinephrine from a glass syringe. The EpiPen® requires two hand operation to remove a cap and arm the device, at the end of which the device needs to be reoriented and properly grasped by the hand that delivers the injection. Several publications describe user error in handling the EpiPen® where the user applies the wrong side of the EpiPen® auto-injector to the subject, and wasting the medication dose toward the opposite side (away from the target injection site).

U.S. Pat. No. 8,425,462 teaches an auto-injector propelled by a $CO_2$ cartridge. The auto-injector has an actuation guard that is removable to allow activation of the device. Two hand operation is required to remove the actuation guard and prepare the device for injection. As a result, it is likely that reorientation of the device and change in hand grasp would be performed during preparation for injection.

U.S. Pat. No. 6,979,316 teaches an auto-injector operated by a spring. A molded safety cover is fitted onto the forward end of the housing and maintains the sterility of the internal components and also prevents inadvertent actuation of the device. The safety cover must be removed from the device before it can be used.

In similar fashion, other auto-injector technologies, in commercial embodiments and in published documentation, require two hand operation to prepare for injection and bare the risk of mishandling for administration.

SUMMARY

According to some embodiments described herein, an auto-injector is described that is activatable to administer a beneficial agent to a subject. The auto-injector is configured to be operable single-handedly, without changing the hand grasp of the auto-injector body, from a pre-used configuration in its storage or carrying package or receptacle, to administration. According to some embodiments described herein, the auto-injector automatically mixes components of the beneficial agent without altering the operation simplicity. According to some embodiments described herein, the auto-injector further comprises an ornamental feature to facilitate tactile and visual recognition of the device. According to some embodiments described herein, a first auto-injector can be stored or carried with a second auto-injector, and the first auto-injector comprises at least one of ornamental, graphical, and color recognition feature allowing a user to at least one of tactile and visually differentiate the first auto-injector from the second auto-injector. According to some embodiments described herein, the auto-injector provides tactile, visual, and audible feedback when it is moved from the pre-use configuration to the armed configuration, from the armed configuration to administration, and/or when administration is completed. Embodiments of the auto-injector described herein is designed to minimize user errors.

According to some embodiments described herein, the auto-injector arrangement comprises (a) an auto-injector comprising an injector body housing a beneficial agent, and (b) an actuator moveably connected to the auto-injector, the actuator comprising an anchoring link adapted to be connected to an anchoring body, wherein when in a first auto-injector arrangement state, the auto-injector is rendered incapable of expelling the beneficial agent, and when in a second auto-injector arrangement state, corresponding to the auto-injector having being moved relative to the anchoring body from the first auto-injector arrangement state, the auto-injector is rendered capable of expelling the beneficial agent.

According to some embodiments described herein, the auto-injector, comprises (a) an injector housing having an injection end, (b) an administration assembly disposed within the injector housing, the administration assembly having a delivery end proximate to the injection end through which a beneficial agent housed within the administration assembly is capable of being expelled, and (c) an actuator moveably connected to the administration assembly, wherein when in a first auto-injector state, the actuator is coupled to the administration assembly such that the delivery end is rendered incapable of being applied to a subject and the administration assembly is rendered incapable of expelling the beneficial agent, and when in a second auto-injector state, corresponding to the actuator having been manipulated from the first auto-injector state, the administration assembly is rendered capable of expelling the beneficial agent, the auto-injector thereafter movable into a third auto-injector state in which the actuator is separated from the auto-injection.

In some embodiments described herein, the auto-injector can be carried in a receptacle in a safe configuration, and is armed when removed from the receptacle. In the safe mode the auto-injector will not activate under any carrying conditions including when it is exposed to external force, shock, vibration, or other environmental condition. When removed from the receptacle the auto-injector changes from the safe configuration to armed configuration. In some arrangements, in the armed configuration the auto-injector is automatically activated by depressing the injection side of the auto-injector against an injection site of a subject. In some arrangements activation of the auto-injector triggers an injection sequence comprising deploying a needle from a concealed position in the auto-injector body, delivering the beneficial agent, and retracting the needle. In some arrangements the auto-injector stores at least two constituents of a beneficial agent, in separated compartments, and the compartments are automatically merged when the auto-injector is removed from the carrying receptacle. The carrying receptacle may by, but not limited to, a carrying case, a pouch, a pocket, a cradle, a hanger, a bracket, a box, a kit, a belt, or any combination thereof, or other carrying receptacles know in the art.

In some embodiments, the auto-injector comprises a removable link having a first end attached to the auto-injector and a second end attached to an attachment point at or in proximity to the carrying receptacle, and the arrangement is such that when the auto-injector is removed from the carrying receptacle the removable link is pulled and causes the auto-injector to arm. After the auto-injector is armed, the removable link is detached either from the attachment point and/or the auto-injector. The removable link may be one of, but not limited to, a strap, a string, a chain a rope, a cable, a combination of the above, or any other linking mechanism known in the art. In some arrangements the auto-injector comprises a removable cap that is attached to the removable link, and the arrangement is such that when the removable link pulls on the removable cap, the removable cap manipulates the auto-injector to an armed configuration, before the cap is removed from the auto-injector. In some arrangements the auto-injector comprises a removable link and at least two constituents of a beneficial agent, separately stored in individual compartments, and the arrangement is such that when the removable link is pulled, the auto-injector is manipulated to merge these compartments. In some arrangements the auto-injector comprises a removable link joined to a removable cap, and at least two constituents of a beneficial agent, separately stored in individual compartments, and the arrangement is such that when the removable link pulls the removable cap, the auto-injector is manipulated to merge these compartments.

In some embodiments described herein, the auto-injector is movable from a safe, pre-use configuration to an armed configuration, and while in the carrying receptacle the auto-injector is maintained in the safe configuration. A spring biases the auto-injector toward the armed configuration such that when the auto-injector is removed from the carrying receptacle the spring moves the auto-injector from a safe configuration to the armed configuration.

In some embodiments described herein, the carrying receptacle is configured in such a way that the hand grasp necessary for removal of the auto-injector from the receptacle is substantially similar to the hand grasp for injection such that the auto-injector can be single-handedly operated without substantially changing the hand grasp, from the removal from the carrying receptacle, all the way to completion of the injection procedure. In some arrangements the carrying receptacle and the removable link are configured in such a way that the hand grasp necessary for removal of the auto-injector from the receptacle is substantially similar to the hand grasp for injection such that the auto-injector can be single-handedly operated without substantially changing the hand grasp, from the removal from the carrying receptacle all the way to completion of the injection procedure. In some arrangements the carrying receptacle, the removable link, and the removable cap are configured in such a way that the hand grasp necessary for removal of the auto-injector from the receptacle is substantially similar to the hand grasp for injection such that the auto-injector can be single-handedly operated without substantially changing the hand grasp, from the removal from the carrying receptacle to completion of the injection procedure.

BRIEF DESCRIPTION OF THE DRAWINGS

FIGS. 2a-2e illustrate a reconstitution arrangement of an auto-injector according to various embodiments described herein;

FIGS. 3a-3d illustrate an auto-injector arrangement comprising an anchoring link according to various embodiments described herein;

FIGS. 12a and 12b illustrate a receptacle comprising a cap, configured for twist-off arming, according to various embodiments described herein;

DETAILED DESCRIPTION

Figures 1A, 1B:
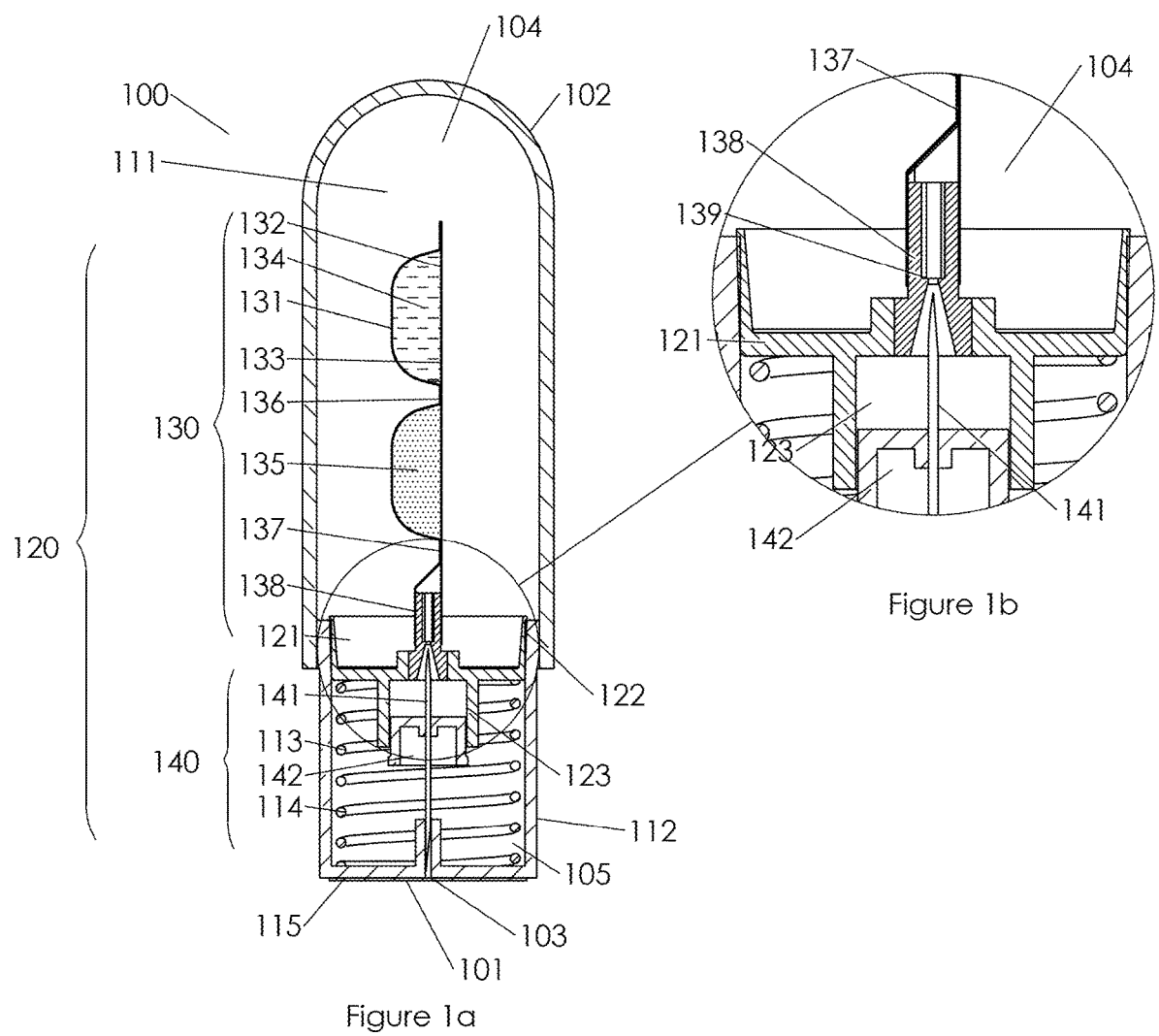
FIGS. 1a-1f illustrate a first arrangement of an auto-injector according to various embodiments described herein and the operation sequence configurations thereof.
Figure 1C:
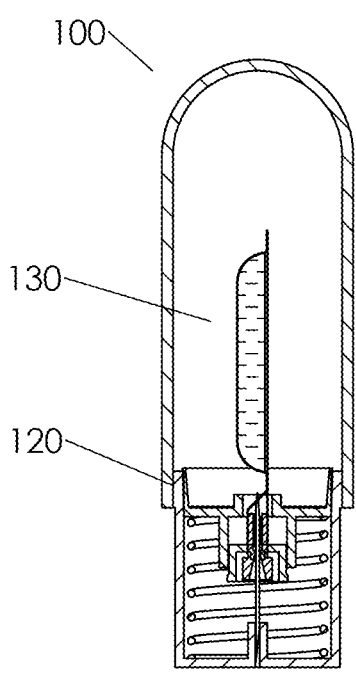
Figure 1D:
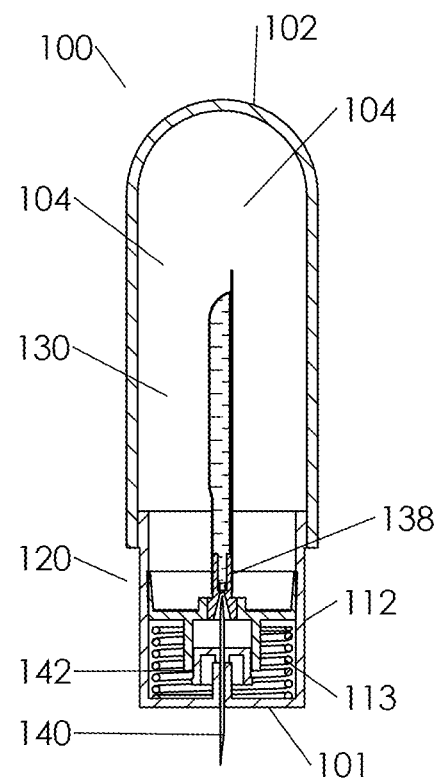
Figure 1E:
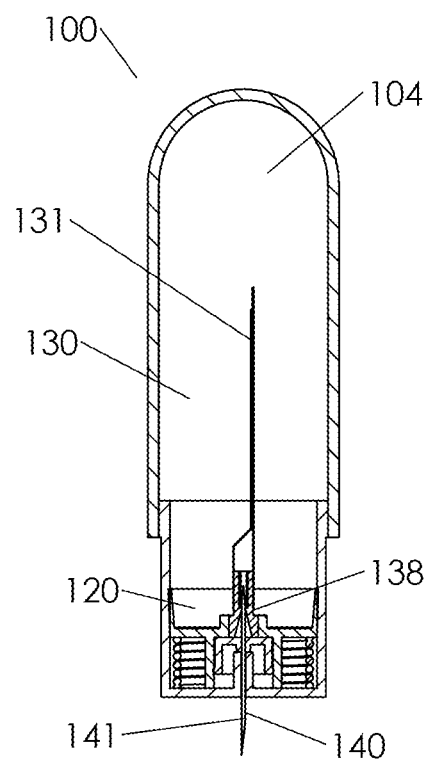
Figure 1F:
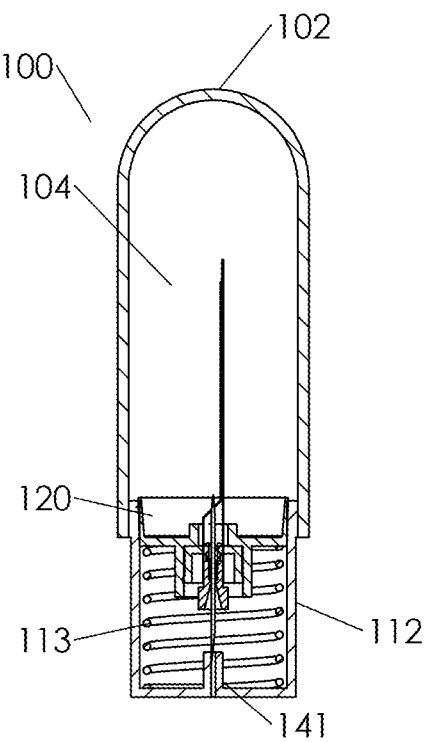

FIGS. 1a-1f illustrate a simplified arrangement of an auto-injector 100 of the present disclosure teaching the basic principles of its construction and operation. FIGS. 1a and 1b illustrate an arrangement of the auto-injector 100 comprising a shell 102 (hereafter, by itself or in combination with other auto-injector elements, sometimes referred to as the auto-injector housing or auto-injector body), and a needle housing 101, together defining the external shell of the auto-injector 100. The auto-injector 100 has a generally elongated cylindrical form comprising a proximal end (hereafter sometimes referred to as the injection end) 101 comprising a needle port 103, and distal end 102, where the auto-injector 100 may be hand grasped during the injection procedure. A movable piston assembly (also referred to as the administration assembly) 120 separates the interior volume of the auto-injector into a pressure chamber 104 and a sterile needle housing 105. The administration assembly 120 comprises a piston 121, a beneficial agent package assembly 130 joined to its distal end, within the pressure chamber 104, and a movable needle assembly 140 joined at its proximal end, within the needle housing 105. The needle assembly 140 comprises a needle 141 comprising a proximal sharp end and a distal sharp end, and a needle hub 142, and is movable between a first pre-use position and a second injection position, as will be detailed in the following Figures. The package assembly 130 comprises a first flexible wall 131 and a second wall 132 joined along their peripheral edges in a permanent seal fashion. The first package wall 131 and the second package wall 132 are further joined across the package to form a first frangible seal 136 defining a first compartment 134 adjacent to a second compartment 135. A second frangible seal 137 separates between the compartments 134-135 and a fitment 138 that is joined to the piston 121. The first compartment 134 and the second compartment 135 may be filled with at least one beneficial agent or constituents thereof. The fitment 138 comprises a membrane section 139 confronting the distal sharp end of the needle 141. A spring 114 biases the piston assembly toward the pressure chamber 104. An adhesive label 115 seals over the needle port 103 to maintain the needle 141 sterile until the time of use. FIG. 1c illustrates a configuration of the auto-injector 100 where the first compartment 134 and the second compartment 135 have been merged, by breaking the first frangible seal 136, allowing the at least first beneficial agent constituent in the first compartment 134 and at least a second constituent in the second compartment 134 to mix and or interact. The package 130 may comprise more than two mergeable compartments. FIG. 1d is showing a configuration of the auto-injector 100 where the second frangible seal (137 in FIG. 1a) of the package assembly 130 has been ruptured establishing fluid communication between the beneficial agent(s) and the fitment 138. FIG. 1d illustrates an injection configuration of the auto-injector 100, wherein pressure is introduced into the pressure chamber 104 in the auto-injector body. The pressure is introduced from a pressure source that when opened creates pressure in the auto-injector body. When the pressure surpasses a first threshold value, the pressure causes the piston to overcome the spring 113 force displacing the needle assembly 120 toward the proximal end 101. The needle assembly 140 moves along with the piston until the needle hub 142 stops against the bottom of the needle housing 112. During usage of the auto-injector 100, in this configuration it is held at the distal end 102 while the proximal end 101 is depressed against an injection site of a subject, such that the proximal end of the needle 141 is inserted into the subject. An arrangement of the pressurizing mechanism of the pressure chamber 104 is shown in following Figures. In FIG. 1e the piston assembly 120 continues its displacement toward the proximal end 101, while the needle assembly 140 is stationary, causing the back end of the needle 142 to pierce the membrane (139 in FIG. 1b) of the fitment 138, thereby establishing fluid communication between the package assembly 130 and the needle 141. The pressure in the pressure chamber 104 causes the first wall 131 to collapse and deliver the beneficial agent(s) through the needle 141. The pressure in the pressure chamber 104 is gradually reduced by releasing the gas within through a bleeding arrangement (not shown). FIG. 1f illustrates a configuration of the auto-injector 100 after the pressure in the pressure chamber 104 has dropped to such a degree that the spring 113 can displace the needle assembly 120 toward the distal end 102 of the auto-injector 100 until the needle is concealed again in the needle housing 112.

Figure 2A:
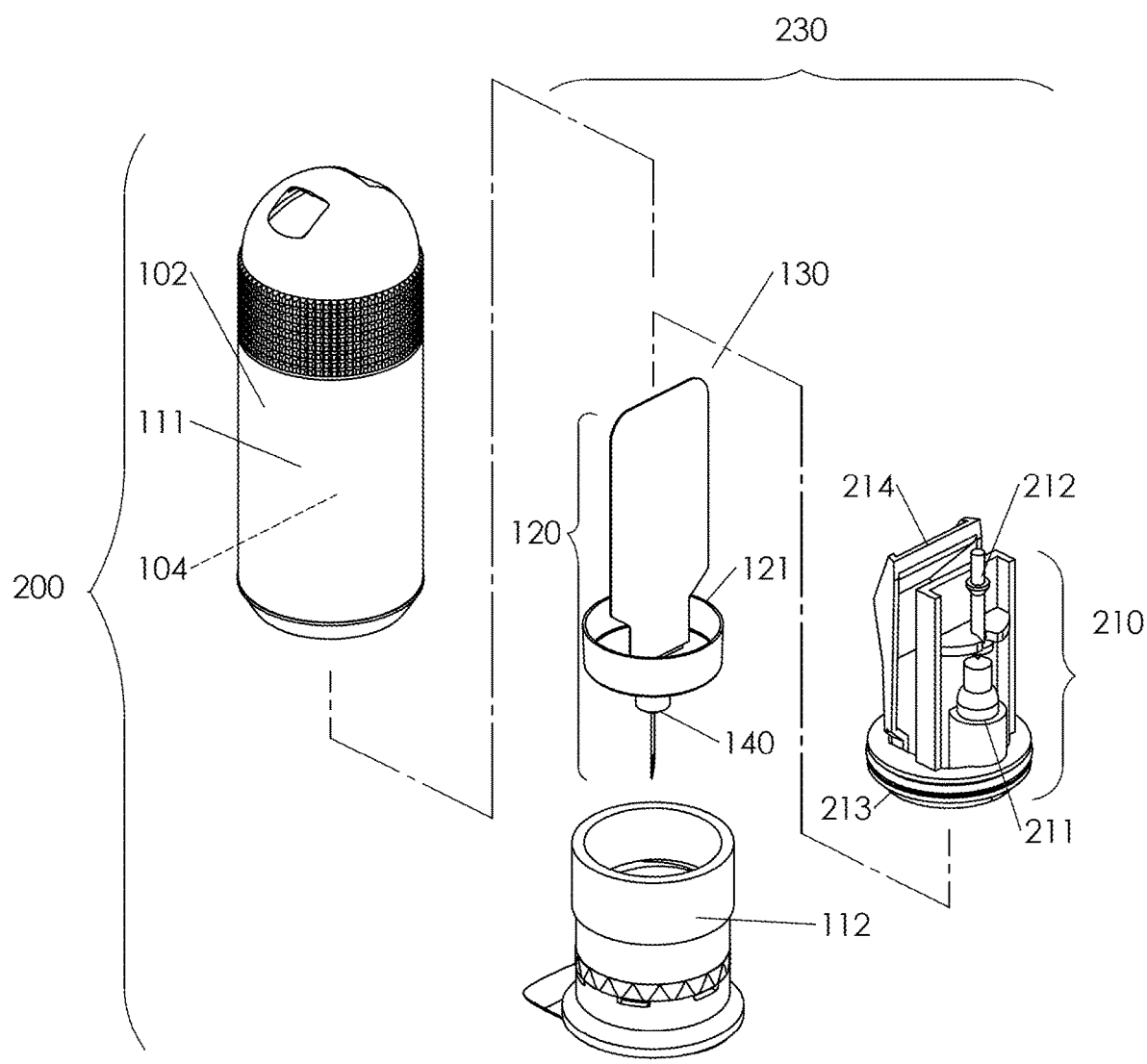
Figure 2E:
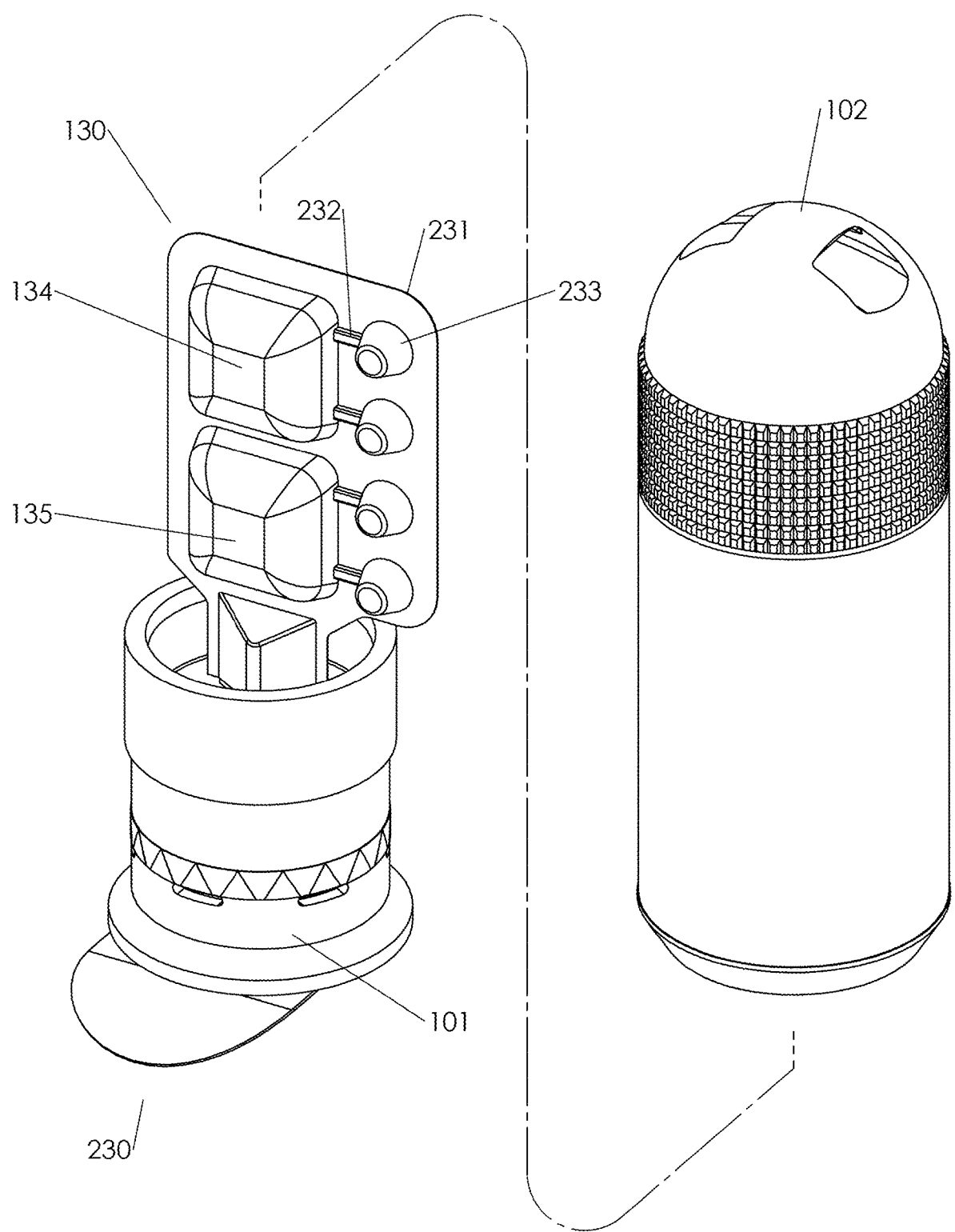

FIG. 2a illustrates an arrangement of an auto-injector 200 comprising an auto-injector body comprising a shell 102 and a needle housing 112 which together form the exterior of the auto-injector 200. A piston assembly 120 is disposed in the auto-injector body (hereafter can be referred to as the auto-injector housing) and comprises a piston 121, accommodating a package assembly 130 at its distal side, and a needle assembly 140 at its proximal side. An actuation assembly 210 is disposed in the pressure chamber 104, comprising a support structure 213 which hold in alignment a pressurized cartridge 211 in a confronting position to a piercing pin 212. The support structure 213 further accommodates a compression panel 214 for manipulating the compartment of the package assembly 130 to merge. FIG. 2b illustrates a cross section of auto-injector 200 in the first auto-injector state (hereafter can be referred to as the pre-use configuration). The compression panel 214 confronts the first compartment 134 on its first side and leans against a cam 221 at its second side. The cam 221 is fixed to the shell 102. A latch feature 222 is also fixed to the shell 102. The pin's 212 sharp end is facing the pierceable region of the pressurized cartridge 211, and is free to move along its axis. However in this configuration nothing can apply an axial force to the pin 212 and hence an accidental piercing of the cartridge 211 is not possible. FIG. 2c illustrates a second auto-injector state and an mixing auto-injector state wherein the shell 102 is extended away from the needle housing 112, causing the cam 221 to push the compression panel 214 which in return depresses the package 130 causing its compartments to merge, and establish fluid communication with the fitment 138. The support structure 213 holds the pin 212 from moving upward while the latch feature 222 moves along with the shell 102, slides over the pin's 212 shaft, and engages with a detent ridge 215 of the pin 212. At this point the pin 212 is retained to the shell 102. A slot 231 in the shell 102 allows connecting an anchoring link (here after sometimes referred to as the anchoring link) such as a strap or other devices to facilitate pulling the shell 102 to the extended position. In FIG. 2d the shell 102 is moved down, carrying along the pin 212 which pierces the pierceable region of the pressurized cartridge 211, thereby pressurizing the pressure chamber 104. The pressurized canister 211 may contain carbon dioxide, nitrogen, argon, or other gasses or supercritical fluids. When the pressure in the pressure chamber 104 exceeds a first threshold value, the force it exerts on the piston 112 overcomes the spring 113 force, moving the piston 112 toward the proximal injection end 101. The needle assembly 140 moves with the piston 121 until it is stopped by the needle housing 101 floor, at which point the needle 141 is fully extend. With the needle assembly 140 now stationary, the pressure in the pressure chamber 104 continues to move the piston 121 down, resulting in a relative movement between the needle assembly 140 and the piston 121, causing the distal end of the needle 141 to pierce the package assembly 130 and establish fluid communication with the beneficial agent. With the pressure chamber 104 still pressurized, the beneficial agent is squeezed out of the package 130 and administered via the needle 141 to a subject. In one arrangement the position of the cam 221 relative to the compression panel 214, and the position of the latch 222 relative to the detent ridge 215 are such, that a first move of the needle housing 112 changes the device 200 to the mixing auto-injector 200 state, where the compartments of the package 130 are merged, and a subsequent second move moves the device 200 to the third auto-injector state (here after sometimes referred to as the armed configuration). This arrangement is particularly beneficial where the beneficial agent is ready for injection only after a certain time from mixing, such that the device can be kept at a safe, unarmed state during mixing. FIG. 2e illustrates the auto-injector 200 in a manufacturing configuration. The needle housing 101 assembly is sterile and ready to fill at the filling site. Special access regions 233 in the package assembly 130 allows the filling machine to fill the package and subsequently seal the channels 232 connecting the access regions 233 and the compartments 134,135. When filling is completed the access regions 233 may be removed and the shell 102 is installed on the needle housing assembly 250. An According to one aspect of the arrangement of FIG. 2a-d, the auto-injector 200 comprises: (a) an injector housing 102 having an injection end 101, (b) an administration assembly 230, comprising the piston assembly 120, the actuation assembly 210, and the needle housing 112, disposed within the injector housing 102, the administration assembly 230 having a delivery end 231 proximate to the injection end 101 through which a beneficial agent housed within the administration assembly 230 is capable of being expelled; when in the auto-injector 200 state illustrated in FIGS. 2a-2b, the administration assembly 230 is rendered incapable of expelling the beneficial agent; and when in the auto-injector 200 state illustrated in FIG. 2c, the administration assembly 230 is rendered capable of expelling the beneficial agent. The administration assembly 230 comprises a first compartment 134 for storing at least a first constituent of the beneficial agent, and at least a second compartment 135 for storing at least a second constituent of the beneficial agent separate from the first constituent; and wherein at the auto-injector state illustrated in FIG. 2c, the first compartment 134 and the at least second compartment 135 are merged.

Figures 3A, 3B, 3C:
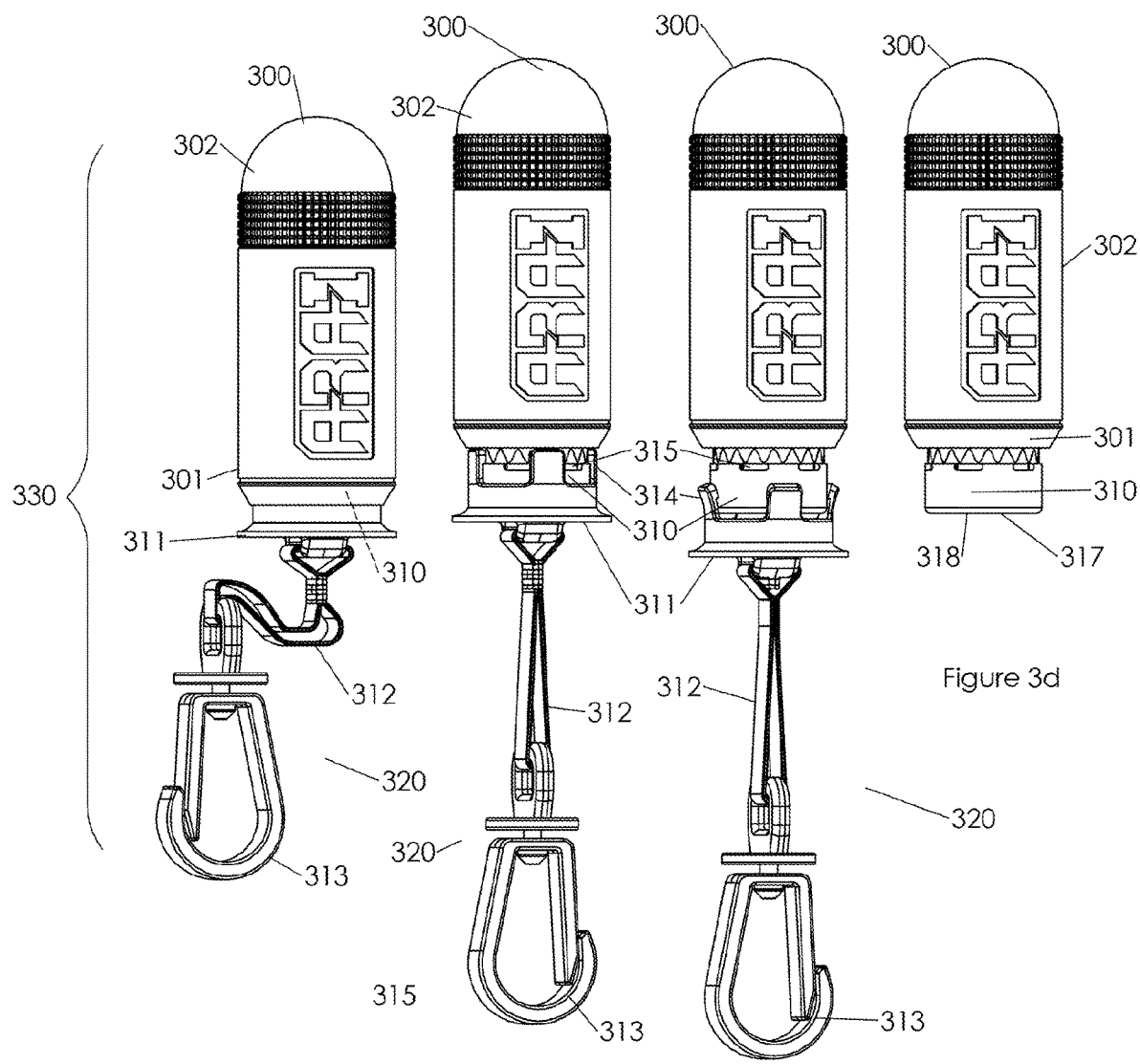

FIG. 3a illustrates an auto-injector arrangement 330 and an auto-injector 300 in the first auto-injector state (hereafter can be referred to as the pre-use configuration of an auto-injector 300) comprising an auto-injector housing comprising a shell 302. An actuator in the form of a removable cap 311 is joined with the proximal end of the administration assembly 310, providing a sterile seal to the needle housing 310. The cap 311 is joined to an anchoring link comprising a strap 312 that terminates with a buckle 313. The cap 311 comprises detent arms (not shown in FIG. 3a), that reach into a gap between the outer diameter of the administration assembly 310 and the inner diameter of the shell 302, and fit in a circumferential recess on the outer diameter of the administration assembly 310 (not shown in FIG. 3a), such that when the strap 312 is pulled, as shown in FIG. 3b, it extends the administration assembly 310 away from the shell 302, thereby moving the auto-injector 300 to a second auto-injector state (hereafter can be referred to as the auto-injector 300 armed configuration). The detent teeth 314 can then be dislodged from the recess 315 in the administration assembly 310, as shown in FIG. 3c, until the cap 311 is completely removed as shown in FIG. 3d. FIG. 3d illustrate the device when it's ready for activation by depressing the administration assembly 310 against a subject. In one arrangement, the auto-injector 300 comprises at least two beneficial agent constituents, housed in the auto-injector body 302, that need to be mixed prior to injection, and a mixing action is initiated when the cap 311 is moved to the mixing auto-injector arrangement state shown in FIG. 3b, and subsequently the device is armed upon a second move when the cap 311 is removed as shown in FIG. 3c. The buckle 313 can be attached to any anchoring body including the auto-injector's carrying receptacle (not shown), or in its vicinity such as a garment of the user.

According to one aspect of the arrangement of FIGS. 3a to 3d, the auto-injector 330 arrangement, comprises: (a) an auto-injector 300 comprising an injector body 302 housing a beneficial agent; and (b) an actuator 311 moveably connected to the auto-injector 300, the actuator comprising an anchoring link 320 adapted to be connected to an anchoring body, wherein: when in a first auto-injector arrangement 330 state, the auto-injector 300 is rendered incapable of expelling the beneficial agent; and when in a second auto-injector arrangement 330 state, corresponding to the auto-injector 300 having being moved relative to the anchoring body from the first auto-injector arrangement 330 state, the auto-injector 300 is rendered capable of expelling the beneficial agent. Moving the actuator from the first auto-injector arrangement 300 state, illustrated in FIG. 3a, to the second auto-injector arrangement 300 state, illustrated in FIG. 3b, comprises moving the actuator 311 relative to the injector housing 302. In one arrangement, the sequence steps illustrated in FIGS. 3b to 3d are combined, such that in the second auto-injector arrangement 300 state the actuator 311 is separated from the auto-injector 300. In one arrangement the anchoring link 320 comprises at least one of a strap, a clip, a chain, a cable, a lanyard, a hook or a combination thereof. In one arrangement, the actuator 311 comprises a cap. In one arrangement, at the first auto-injector arrangement 300 state, illustrated in FIG. 3a, the cap isolates at least a portion of the auto-injector 300 from the surrounding environment. In one arrangement the anchoring body comprises an auto-injector receptacle inside of which, in the first auto-injector arrangement state, at least a portion of the auto-injector is accommodated, and wherein the receptacle comprises at least one of an enclosure, a package, a bag, a pouch, a pocket, a belt, a container, a holster, a cradle, a kit, a garment, or any combination thereof. The relative movement of the actuator 311 relative to the anchoring body, to move the auto-injector arrangement from 300 from the first auto-injector arrangement state to the second auto-injector arrangement state, comprises linear motion. In one arrangement the injector body 302 comprises a first compartment for storing at least a first constituent of the beneficial agent, and at least a second compartment for storing at least a second constituent of the beneficial agent separate from the first constituent; and when in a mixing auto-injector arrangement state, corresponding to the auto-injector 300 having been moved relative to the anchoring body from the first auto-injector arrangement 330 state, the first compartment and the at least second compartment are merged and the auto-injector 300 is rendered incapable of expelling beneficial agent. In one arrangement transitioning the auto-injector arrangement 330 from the first auto-injector arrangement 330 state to the mixing auto-injector arrangement 330 state comprises a first movement of the auto-injector 300 relative to the anchoring body and transitioning the auto-injector arrangement 330 from the mixing auto-injector arrangement 330 state to the second auto-injector arrangement 330 state comprises a second movement of the auto-injector 300 relative to the anchoring body. In one arrangement the mixing auto-injector arrangement 300 state and the second auto-injector arrangement state 330 are the same. In one arrangement the actuator 311 is separated from the auto-injector 300 in the second auto-injector arrangement 330 state. In one arrangement the auto-injector 300 is removed from the receptacle in the second auto-injector arrangement 330 state. In one arrangement the auto-injector further comprises a compressed gas source that when opened provides gas pressure within the injector body 302 to expel the beneficial agent, and wherein the compressed gas source is incapable of opening in the first auto-injector arrangement 330 state, and the compressed gas source is capable of being opened in the second auto-injector arrangement 330 state. According to one aspect of the auto-injector arrangement 330, the injector body 302 comprises an activation member 317, extending therefrom, which is the delivery end of the administration assembly 310, that when moved toward the injector body 302, activates the auto-injector 300 to expel the beneficial agent, and wherein the actuator 311 impedes the activation member 317 from moving toward the injector body 302 in the first auto-injector arrangement 330 state, illustrated in FIG. 3a. The activation member 317 comprises a delivery end 318 from where the beneficial agent is expelled.

According to one aspect of the auto-injector arrangement 330, the auto-injector 300, comprises: (a) an injector housing 302 having an injection end 301; (b) an administration assembly 310 disposed within the injector housing 302, the administration assembly 310 having a delivery end 318 proximate to the injection end 301 through which a beneficial agent housed within the administration assembly 310 is capable of being expelled; and (c) an actuator 311 moveably connected to the administration assembly 310, wherein: when in a first auto-injector 300 state, illustrated in FIG. 3a the actuator 311 is coupled to the administration assembly 310 such that the delivery end 318 is rendered incapable of being applied to a subject and the administration assembly 310 is rendered incapable of expelling the beneficial agent; and when in a second auto-injector 300 state, illustrated in FIG. 3b, corresponding to the actuator 311 having been manipulated from the first auto-injector 300 state, the administration assembly 310 is rendered capable of expelling the beneficial agent, the auto-injector 300 thereafter movable into a third auto-injector 300 state, illustrated in FIG. 3d, in which the actuator 311 is separated from the auto-injector. Manipulating the actuator 311 from the first auto-injector 300 state to the second auto-injector 300 state comprises moving the actuator relative to the injector housing 302. The actuator 311 is moveably connected to the delivery end 318 of the administration assembly 311, but it would be obvious to one skilled in the art that the actuator 311 can be connected to the administration assembly in other locations, such as the opposite end of the injection end 301. In one arrangement the administration assembly 310 comprises a first compartment for storing at least a first constituent of the beneficial agent, and at least a second compartment for storing at least a second constituent of the beneficial agent separate from the first constituent; wherein at the second auto-injector state, the first compartment and the at least second compartment are merged.

Figures 4A, 4B, 4C:
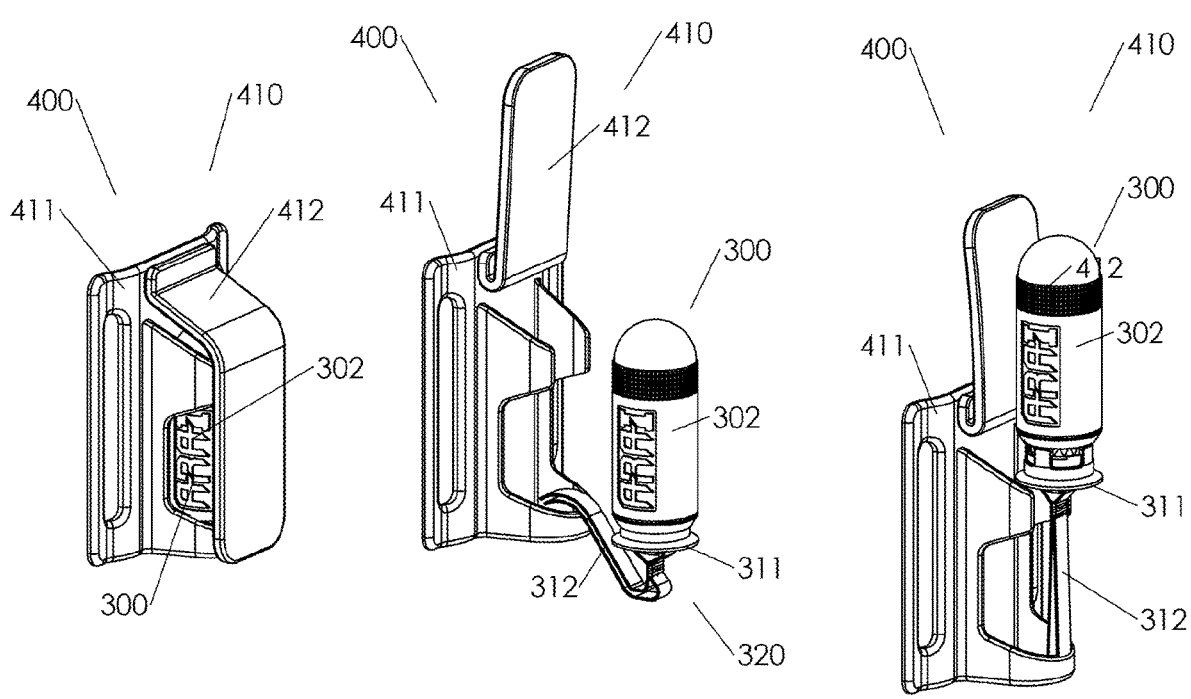
FIGS. 4a-4c illustrate an auto-injector arrangement comprising a receptacle according to various embodiments described herein.

FIGS. 4a and 4b illustrate the auto-injector 300 nested in a carrying receptacle in a form of a cradle or holster 411. The cradle comprises a protective cover 412 and it can be strapped down to a person's arm, belt, leg, or a package, bag etc. The cradle 411 is configures such that the auto-injector 300 can be single handedly removed from the cradle 411. The auto-injector may be removed by holding the shell (also referred to as the auto-injector housing) 302 in substantially the same hand grasp that the auto-injector 300 should be held for activation, hence the auto-injector 300 can be removed from the carrying receptacle 311, pulled off from the strap 312 for arming, and be depressed onto the injection site in a single action, single handedly, at a substantially similar hand grasp of the shell 302.

According to one aspect of the auto-injector arrangement 400, the auto-injector arrangement 400, comprises: (a) an auto-injector 300 comprising an injector body 302 housing a beneficial agent; and (b) an actuator 311 moveably connected to the auto-injector 300, the actuator 311 comprising an anchoring link 320 connected to an anchoring body 410 comprising a holster 411; wherein: when in a first auto-injector arrangement 400 state, illustrated in FIGS. 4a and 4b, the auto-injector is rendered incapable of expelling the beneficial agent; and when in a second auto-injector arrangement 400 state, corresponding to the auto-injector 300 having being moved relative to the anchoring body 410, as illustrated in FIG. 4c, from the first auto-injector arrangement 400 state, the auto-injector 300 is rendered capable of expelling the beneficial agent. Moving the actuator 311 from the first auto-injector arrangement 400 state to the second auto-injector arrangement 400 state comprises moving the actuator 311 relative to the injector body 302. In one arrangement, in the second auto-injector arrangement 400 state, the actuator 311 is separated from the auto-injector 300. In one arrangement the anchoring link 320 comprises at least one of a strap, a clip, a chain, a cable, a lanyard, a hook or a combination thereof. The actuator 311 comprises a cap, and in one arrangement, at the first auto-injector arrangement 400 state, the cap isolates at least a portion of the auto-injector 300 from the surrounding environment. The anchoring body 410 comprises an auto-injector receptacle inside of which, in the first auto-injector arrangement 400 state, at least a portion of the auto-injector 300 is accommodated. In some arrangements the receptacle comprises at least one of an enclosure, a package, a bag, a pouch, a pocket, a belt, a container, a holster, a cradle, a kit, a garment, or any combination thereof. The relative movement of the auto-injector 300 relative to the anchoring body 410, from the first auto-injector arrangement 400 state to the second auto-injector arrangement 400 state, comprises linear motion. In one arrangement the injector body 302 comprises a first compartment for storing at least a first constituent of the beneficial agent, and at least a second compartment for storing at least a second constituent of the beneficial agent separate from the first constituent; and when in a mixing auto-injector arrangement 400 state, corresponding to the auto-injector 300 having been moved relative to the anchoring body 410 from the first auto-injector arrangement 400 state, the first compartment and the at least second compartment are merged and the auto-injector 300 is rendered incapable of expelling beneficial agent. In one arrangement transitioning the auto-injector arrangement 400 from the first auto-injector arrangement 400 state to the mixing auto-injector arrangement 400 state comprises a first movement of the auto-injector 300 relative to the anchoring body 410, and transitioning the auto-injector arrangement from the mixing auto-injector arrangement 400 state to the second auto-injector arrangement 400 state comprises a second movement of the auto-injector 300 relative to the anchoring body 410. In one arrangement the mixing auto-injector arrangement 400 state and the second auto-injector arrangement 400 state are the same. In one arrangement the actuator 311 is separated from the auto-injector 300 in the second auto-injector arrangement 400 state. In one arrangement the auto-injector 300 is separated from the receptacle 400 in the second auto-injector arrangement 400 state. In one arrangement the auto-injector 300 further comprises a compressed gas source that when opened provides gas pressure within the injector body 302 to expel the beneficial agent, and wherein the compressed gas source is incapable of opening in the first auto-injector arrangement 400 state, and the compressed gas source is capable of being opened in the second auto-injector arrangement 400 state. In one arrangement the injector body 302 further comprises an activation member extending there from that, when moved toward the injector body 302, activates the auto-injector to expel the beneficial agent, and wherein the actuator 311 impedes the activation member from moving toward the injector body 302 in the first auto-injector arrangement 400 state. In one arrangement the activation member comprises an injection end from where the beneficial agent is expelled.

According to one aspect of the auto-injector arrangement 400, the auto-injector 300 comprises: (a) an injector housing 302 having an injection end 301; (b) an administration assembly disposed within the injector housing, the administration assembly having a delivery end proximate to the injection end through which a beneficial agent housed within the administration assembly is capable of being expelled; and (c) an actuator 311 moveably connected to the administration assembly, wherein: when in a first auto-injector 300 state, the actuator 311 is coupled to the administration assembly 310 such that the delivery end is rendered incapable of being applied to a subject and the administration assembly is rendered incapable of expelling the beneficial agent; and when in a second auto-injector 300 state, corresponding to the actuator 311 having been manipulated from the first auto-injector 300 state, the administration assembly is rendered capable of expelling the beneficial agent, the auto-injector 300 thereafter movable into a third auto-injector 300 state in which the actuator 311 is separated from the auto-injector. Manipulating the actuator 311 from the first auto-injector 300 state to the second auto-injector 300 state comprises moving the actuator 311 relative to the injector housing. The actuator 311 is moveably connected to the delivery end of the administration assembly. In one arrangement the administration assembly comprises a first compartment for storing at least a first constituent of the beneficial agent, and at least a second compartment for storing at least a second constituent of the beneficial agent separate from the first constituent; and wherein at the second auto-injector 300 state, the first compartment and the at least second compartment are merged.

Figure 5A:
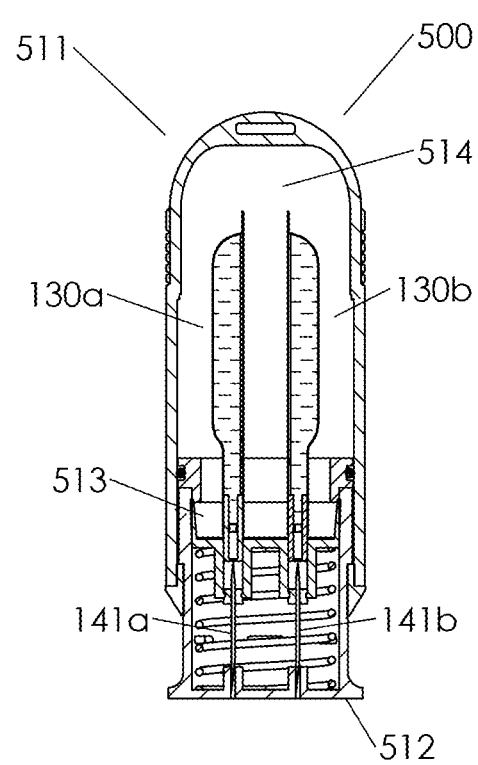
FIGS. 5a and 5b illustrate an auto-injector for simultaneous injections according to various embodiments described herein.
Figure 5B:
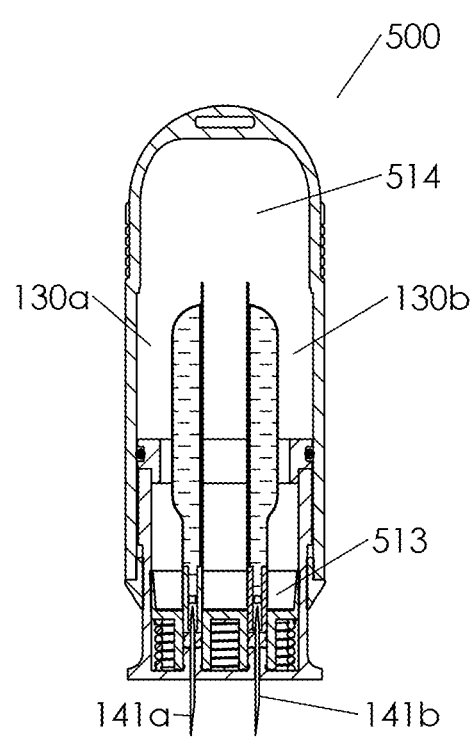

FIGS. 5a and 5b illustrate another arrangement of an auto-injector 500 where the piston 513 accommodates a first beneficial agent package assembly 130a, confronting a first needle 141a, and a second beneficial agent package assembly 130b confronting a second needle 141b. Each beneficial agent package assembly and needle assembly set is operable in the same manner as the auto-injector arrangements 100, 200, 300 described in earlier Figures, such that two injections can be given simultaneously from the auto-injector 500 without changing the operation mode or the product 500 complexity. FIG. 5a illustrates the auto-injector 500 in an armed configuration and FIG. 5b illustrates the auto injector 500 when it is activated. In one arrangement at least one of beneficial agent package assemblies 130a and 130b comprises more than one compartment that are merge at or prior to the arming step.

According to one aspect of FIGS. 5a-5b, the auto-injector 500 is adapted for delivering to a patient at least a first beneficial agent and a second beneficial agent, comprising: (a) an auto-injector body 511 comprising an injection end 512, (b) a piston 513 disposed in the auto-injector body 511 to form a pressure chamber 514, the piston 513 is moveable from a pre-use position to a deployed position (c) a first beneficial agent communicable with a first administration device 141a is connected to the piston 153, (d) a second beneficial agent communicable with a second administration device 141b is connected to the piston 153, wherein when pressure is applied in the pressure chamber 514 the piston 513 moves to deploy the first and second administration devices 141a and 141b through the injection end 512, and the first and second beneficial agents are administered through their respective administration devices.

Figures 6A, 6B, 6C:
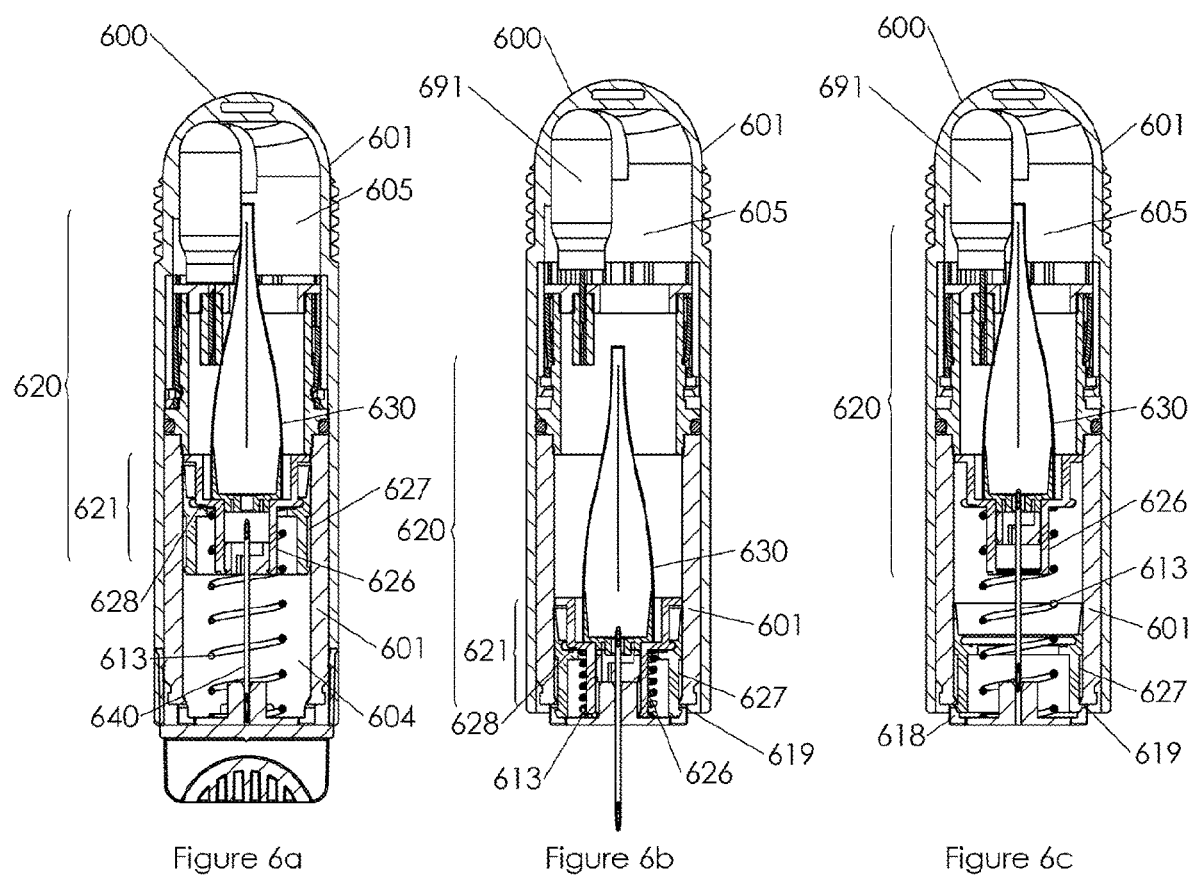
FIGS. 6a-6c illustrate an arrangement of an auto-injector comprising a cap and a tube package according to various embodiments described herein.

FIGS. 6a-6c illustrate another arrangement of the auto-injector 600, activatable to administer a beneficial agent to a subject. FIG. 6a illustrates the auto-injector 600 at a first auto-injector state (here after sometimes referred to as the pre-use configuration). An administration assembly 620 (also referred to as the carriage assembly) comprises the package assembly 630, piston 621, and a needle assembly 640. The package assembly 630 comprises a collapsible tube. The piston 621 comprises a piston core component 626 and a piston skirt component 627, that are latched together via a lateral ridge and groove joint. This joint is substantially fluid tight seal but for a bleeding passageway 628 formed there between to deplete the pressure from the pressure chamber 605 after the device 600 has been activated. The bleeding passageway 628 is formed as a torturous path (such as a labyrinth) that prevents bacteria and contamination from reaching into sterile needle chamber 604 before use. The spring 613 biases the piston core 626 toward the pressure chamber 605. In another arrangement the bleeding passageway is configured such that it only opens when the piston is moved, for example by providing an inward protrusion (such as a rib) that comes off the needle housing 601 wall and interrupts the seal of the piston skirt 627 against that wall, when the piston 621 reaches that protrusion as it travels down. FIG. 1b illustrates the device 600 when activated where the cartridge 691 has been ruptured, and, after exceeding a first pressure threshold value, the pressure in the pressure chamber 605 has driven down the piston assembly 621 toward the proximal end of the device 600. The pressured gas in the pressure chamber 605 is depleting through the bleeding passageway 628. The base of the piston skirt 627 is latched with a detent ridge 619 inwardly facing from the needle housing 601 wall. FIG. 6c illustrates the auto-injector 600 after the pressure in the pressure chamber has dropped to below a second threshold value where the spring 613 was able to release the piston core 626 from the piston skirt 627, and retract the piston core 626 back toward the pressure chamber 605, carrying along the administration assembly 620 (except for the skirt 627). The piston skirt 627 remains latched at the bottom position. By separating the piston core 626 from the skirt 627 the pressure in the pressure chamber 605 is instantly vented through opening 618 in the needle housing 601, allowing abrupt retraction of the administration assembly 620. The opening 618 allows inspection that the auto-injector 600 has been operated by viewing the piston skirt 627 through this opening 618.

Figures 7, 8, 9, 10:
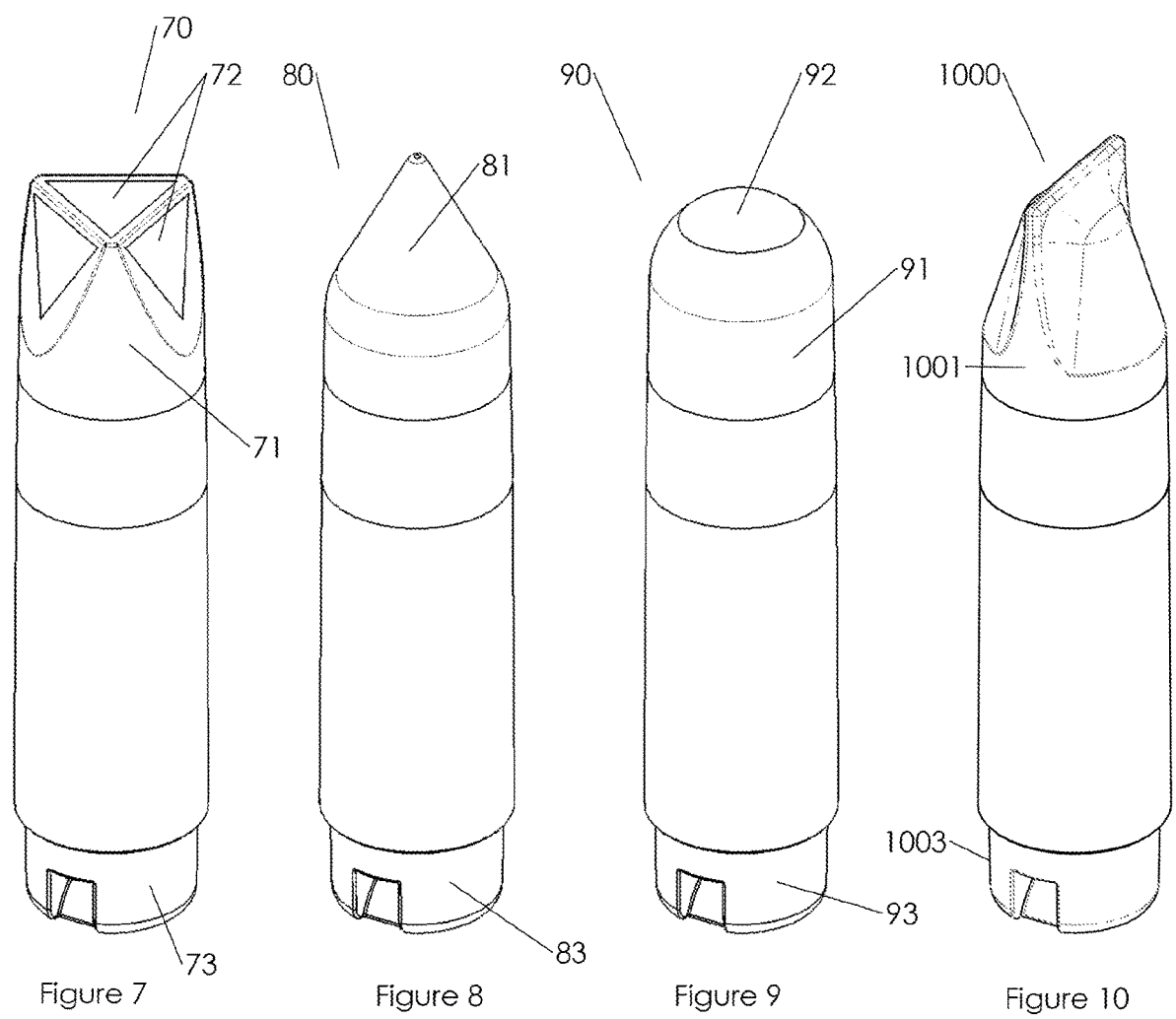
FIG. 7 illustrates an auto-injector with a tactile and visual distinguishable ornamental end piece according to various embodiments described herein.
FIG. 8 illustrates an auto-injector with another tactile and visual distinguishable ornamental end piece according to various embodiments described herein.
FIG. 9 illustrates an auto-injector with yet another tactile and visual distinguishable ornamental end piece according to various embodiments described herein.
FIG. 10 illustrates an auto-injector with still another tactile and visual distinguishable ornamental end piece according to various embodiments described herein.

FIG. 7 illustrates an auto-injector 70 for delivering a first beneficial agent to a subject, comprising an auto-injector body having an elongated shape, comprising an injection end 73 and a distal end 71 opposite to the injection end 71. The distal end has a tactilely distinguishable triangular shape. The auto-injector 70 may be intended to be stored, or carried adjacent to at least a second auto-injector and the distal end 71 shape allows for the user to tactilely distinguish the auto-injector 70 from the at least a second auto-injector, for delivering a second beneficial agent, with a different distal end shape. The auto-injector 70 further comprises graphics 72 of triangular shape which allow a visual recognition of the auto-injector that corresponds to the tactile recognition of the auto-injector 70. The end piece 71 may also be distinguished from other auto-injectors by the color of the distal end 71. The auto-injector 70. In one arrangement the injection end 73 comprises a tactilely, graphical or color features that allows distinguishing the auto-injector 70 from other auto-injectors. In one embodiment at least one of the distinguishing features of the injection end correlate to a distinguishing feature of the distal end. In one arrangement the injection 73 comprises a cap that bares the distinguishing feature. The distal end 71 may be a cap mounted over the auto-injector 70 body.

FIGS. 8, 9, and 10 illustrates auto-injectors with distal ends of different shapes. FIG. 7 illustrates an auto-injector 70 comprising an ornamental end piece 71 comprising a triangular shape. The end piece 71 further comprises printed, stacked-on, or embossed triangular graphics 72 that resemble the triangular shape of the end piece 72. Resembling. FIG. 8 illustrates an auto-injector 80 comprising an ornamental end piece 81 comprising a pointed shape. FIG. 9 illustrates an auto-injector 90 comprising an ornamental end piece 91 comprising a rounded shape. The distal end of FIG. 9 comprises graphic 92 of a circular shape that correlates to the spherical shape of the distal end 91. FIG. 10 illustrates an auto-injector 1000 comprising an ornamental end piece 1001 comprising a flat screwdriver head shape. It would be obvious to one skilled in the art that corresponding ornamental shapes and graphics can be applied to the opposite ends 73, 83, 93, and 1003 of auto-injectors 70, 80, 90, and 1000 respectively. According to one aspect of the auto-injectors 70,80,90, and 1000, a first auto-injector for delivering at least a first beneficial agent intended to be carried or stored adjacent to at least a second auto-injector for delivering at least a second beneficial agent, comprising a generally elongated body comprising an injection end 73, 83, 93, and 1003, and a distal end 71, 81, 91, and 1001 opposite to the injection end, where at least one of said ends comprises a tactile distinguishable shape from the at least one end of the second auto-injector. According to another aspect of FIGS. 7,8,9, and 10, a set of at least a first and a second auto-injectors, each comprising a generally elongated body comprising an injection end 73, 83, 93, and 1003, and a distal end 71, 81, 91, and 1001 opposite to the injection end, at least one of said ends comprises a shape, where said shape of the first auto-injector is tactilely distinguishable from the shape of the at least second auto-injector. The end of the first auto-injector can be distinguished from the at least second auto-injector by at least one of a color, color pattern, and graphics. In one arrangement the auto-injector at least one of the injection end and the distal end comprises a cap and the shape is in the cap. The ornamental shapes can be at least one of a dome, a circle, a triangle, a square, a flat screwdriver head, a Philips screwdriver head, a star, a chess rook, a cone, or a combination or a blend of the formers. The shape and the graphics substantially represent the same shape. In some arrangements the ornamental shape comprises at least one of an indentations, a neck, a recess, through hole, or a blend or a combination of the formers. In some arrangements the shape comprises at least one of indentations, recesses, grooves, notches, or a combination or blend of the formers, arranged in a circumferential, longitudinal, or radial pattern, or a combination or a blend of the above.

Figure 11A:
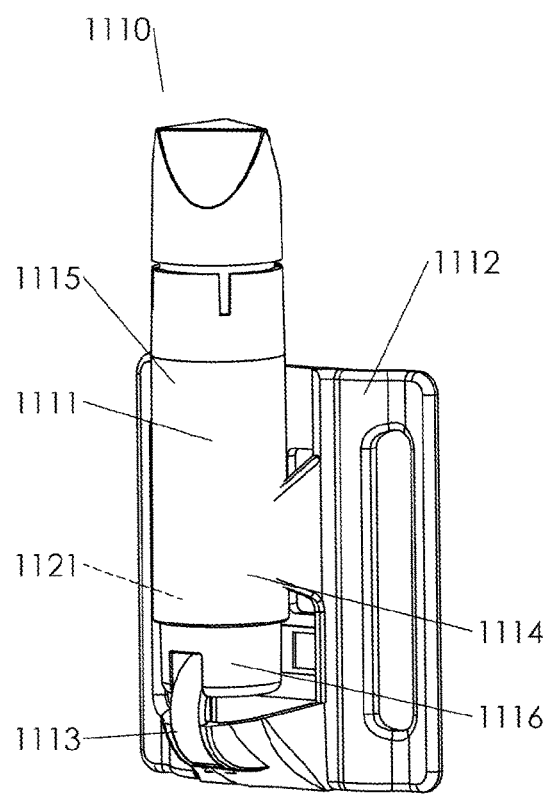
FIGS. 11a-11f illustrate an auto-injector arrangement comprising an anchoring link and a receptacle, configured for a single hand operation, according to various embodiments described herein.
Figure 11B:
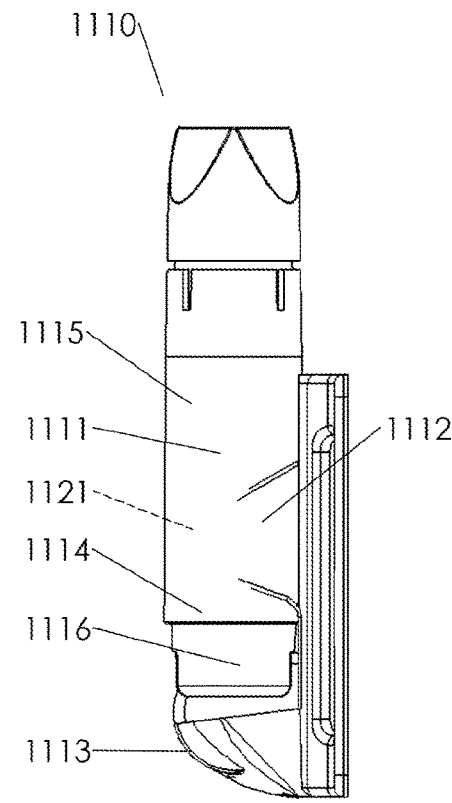
Figure 11C:
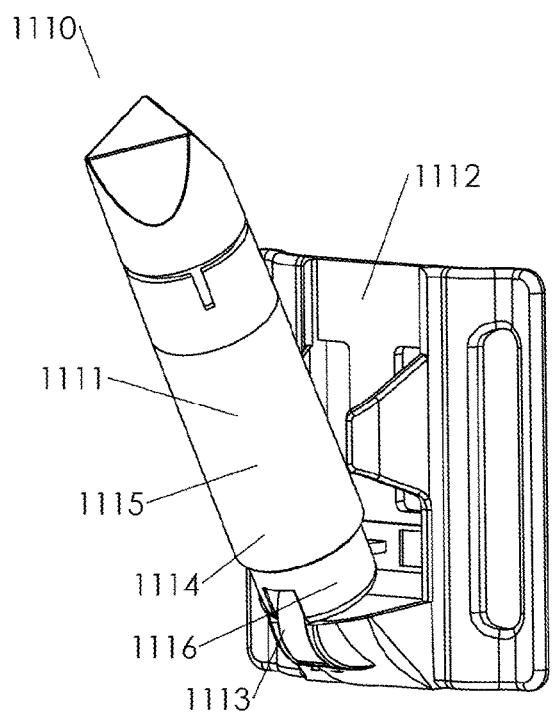
Figure 11D:
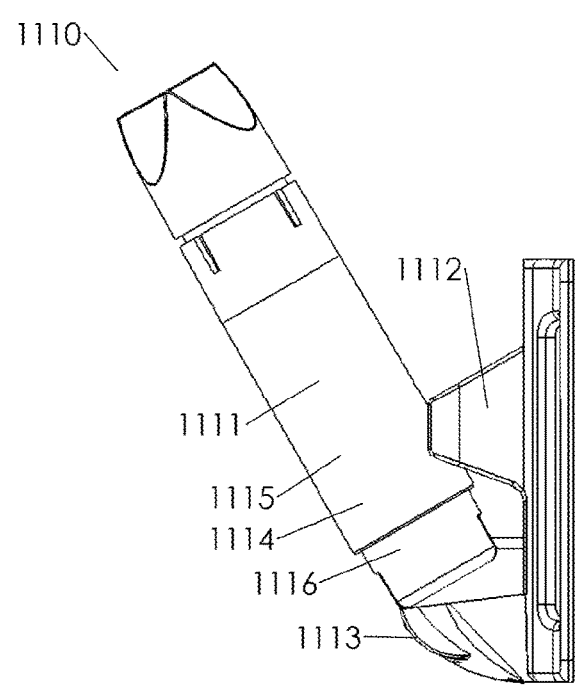
Figure 11E:
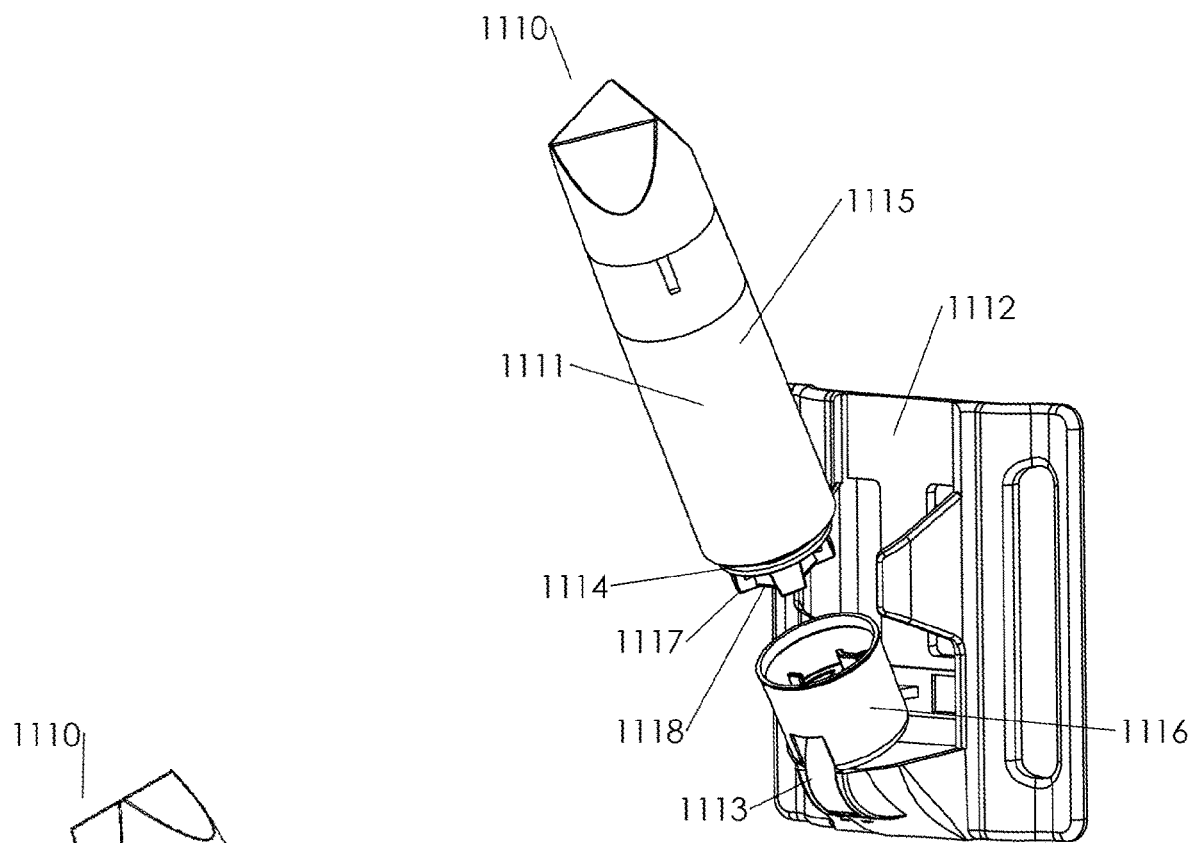
Figure 11F:
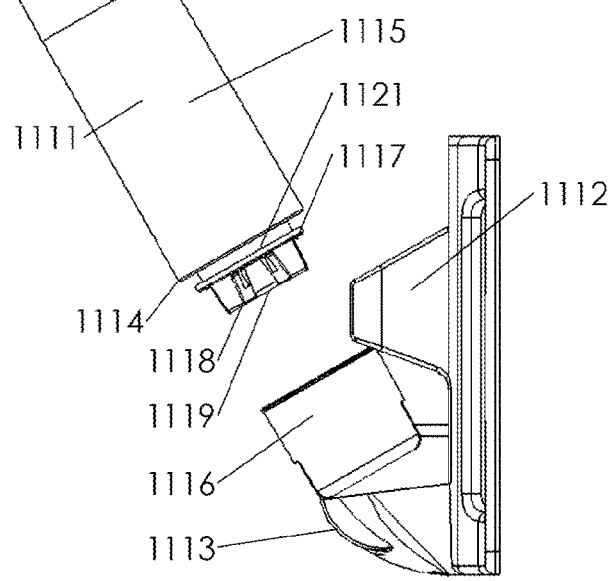

FIG. 11*a* to FIG. 11*f* illustrate an auto-injector arrangement 1110 activatable to deliver a beneficial agent to a subject by an operator, comprising an auto-injector 1115 comprising an auto-injector body 1111 (hereafter can be referred to as auto-injector housing 1111) comprising an injection end 1114, and an anchoring body comprising a receptacle 1112, in a form of a holster, for accommodating therein at least a portion of the auto-injector body 1111 before use. The receptacle 1112 can be mounted or otherwise joined to a belt, a garment, a gear, a bag, a package. FIGS. 11*a* and 11*b* illustrate the auto-injector arrangement 1110 at a first configuration wherein the auto-injector body 1111 seats close to the holster 1112 and, when worn on a belt or other garment or gear, it is substantially protected from accidental impact or interference. FIGS. 11*c* and 11*d* illustrate the auto-injector arrangement 1110 at a second configuration where the auto-injector body 1111 is tilted away from the holster 1112 to allow accessing the auto-injector body 1111 by the operator allowing accessibility for a firm hand grip. The arrangement is such that the auto-injector body 1111 is manipulable relative to the receptacle 1112 from a first configuration, shown in FIGS. 11*a* and 11*b*, where the auto-injector body 1111 is substantially protected from physical interferences (such as accidental and unintentional manipulation), to a second position where the auto-injector body 1111 is partially removed, and substantially extended from the receptacle 1112 to facilitate the operator hand grasp of the auto-injector body 1111. According to one aspect of the present disclosure, the auto-injector is single handedly operable from a pre-use configuration to activation avoiding hand repositioning, thereby reducing the risk of accidentally dropping the device or disorienting it for activation. In the second configuration the device can be confidently hand grasped in the position for activation. In one arrangement the auto-injector 1115 in manipulable from a first auto-injector state (may be referred to as the pre-use configuration), where activation is disabled, to second auto-injector state (may also be referred to as an armed configuration), where activation is enabled, by a relative movement between the auto-injector body 1111 and the receptacle 1112. The arrangement is such that the second configuration facilitates the operator manipulation of the device from the first auto-injector state to the second auto-injector state. In one arrangement the first and second configuration the activation of the device 1110 is disabled. The anchoring body 1112 is not limited to a holster fashion and can be fitted for a particular application, carrying or storing consideration, and may be of different forms and fashions including a package, a bag, a pouch, a pocket, a container, a cradle, a closure, and a cap, or any combination of the above. In one embodiment the movement of the auto-injector 1115 from the anchoring body 1112 comprises axial movement. FIGS. 11*a-f* further illustrate an actuator 1116 comprising an anchoring link 1113 communicating between the anchoring body 1112 and the auto-injector 1115, to facilitate manipulation of the auto-injector 1115. The actuator 1116 is in a form of a cap that extends from the auto-injector body 1111, and covers the injection end of the auto-injector. In FIGS. 11*e* and 11*f* the device 1111 is armed by pulling the auto-injector 1115 away from the actuator 1116 which remains connected to the anchoring body 1112 via anchoring link 1113. The anchoring link 1113 form is not limited to that shown in this figure and can comprise at least a closure, a strap, a clip, a chain, a cable, lanyard, or a combination of the formers. In one embodiment, at the first configuration the auto-injector 1115 is in the first auto-injector state and cannot be moved to the second auto-injector state (armed configuration) without first moving to the second configuration.

According to one aspect of FIGS. 11*a-f*, the auto-injector arrangement 1110 is activatable to deliver a beneficial agent to a subject by an operator. The auto-injector arrangement 1110 comprises: (a) an auto-injector 1115 comprising an auto-injector body 1111 comprising an injection end 1114, and (b) an anchoring body 1112 comprising a receptacle for accommodating at least a portion of the auto-injector body therein before use, the arrangement is such that the auto-injector 1115 is manipulable relative to the anchoring body 1112, from a first position where the auto-injector body is substantially protected from physical interferences (such as accidental and unintentional manipulation), and a second position where the auto-injector 1115 is substantially extended from the anchoring body 1112 to facilitate the operator hand grasp of the auto-injector body 1111. The auto-injector arrangement 1115 is further manipulable from a first auto-injector 1115 state (pre-use configuration), where activation is disabled, to a second auto-injector 1115 state (an armed configuration), where activation is enabled, and where the arrangement is such that the second configuration facilitates the operator manipulation of the auto-injector 1115 from the first auto-injector state to the second auto-injector state. In one arrangement at the first and the second configurations, the auto-injector 1115 activation is disabled. In one arrangement the auto-injector 1115 is moved from the first auto-injector state (the pre-use configuration) to the second auto-injector state (armed configuration) when it is separated from the anchoring body 1112.

According to one aspect of FIGS. 11e and 11f, the auto-injector arrangement 1110, comprises: (a) an auto-injector 1115 comprising an injector body 1111 housing a beneficial agent; and (b) an actuator 1116 moveably connected to the auto-injector 1115, the actuator comprising an anchoring link 1113 adapted to be connected to an anchoring body 1112, wherein: when in a first auto-injector arrangement 1110 state, the auto-injector 1115 is rendered incapable of expelling the beneficial agent; and when in a second auto-injector arrangement 1110 state, corresponding to the auto-injector 1115 having being moved relative to the anchoring body 1112 from the first auto-injector arrangement 1110 state, the auto-injector 1115 is rendered capable of expelling the beneficial agent. Moving the auto-injector 1115 from the first auto-injector arrangement state 1110 to the second auto-injector arrangement 1110 state further comprises moving the actuator 1116 relative to the injector housing 1112. In one arrangement, in the second auto-injector arrangement 1110 state the actuator 1116 is separated from the auto-injector 1115. In one arrangement the anchoring link 1113 comprises at least one of a strap, a clip, a chain, a cable, a lanyard, a hook or a combination thereof. The actuator 1113 comprises a cap, and in one arrangement, at the first auto-injector arrangement 1110 state, the cap 1113 isolates at least a portion of the auto-injector 1115 from the surrounding environment. The anchoring body 112 comprises an auto-injector receptacle in a form of a holster, inside of which, in the first auto-injector arrangement 1110 state, at least a portion of the auto-injector 1115 is accommodated. In some arrangement the receptacle 1112 comprises at least one of an enclosure, a package, a bag, a pouch, a pocket, a belt, a container, a holster, a cradle, a kit, a garment, or any combination thereof. In one arrangement the injector body 1111 comprises a first compartment for storing at least a first constituent of the beneficial agent, and at least a second compartment for storing at least a second constituent of the beneficial agent separate from the first constituent; and when in a mixing auto-injector arrangement state, corresponding to the auto-injector 1115 having been moved relative to the anchoring body 1112 from the first auto-injector arrangement 1110 state, the first compartment and the at least second compartment are merged and the auto-injector 1115 is rendered incapable of expelling beneficial agent. In one arrangement transitioning the auto-injector arrangement 1110 from the first auto-injector arrangement state to the mixing auto-injector arrangement state comprises a first movement of the auto-injector 1115 relative to the anchoring body 1112 and transitioning the auto-injector arrangement 1110 from the mixing auto-injector arrangement to the second auto-injector arrangement state comprises a second movement of the auto-injector 1115 relative to the anchoring body 1112. In one arrangement the mixing auto-injector arrangement 1110 state and the second auto-injector arrangement 1110 state are the same. In one arrangement the actuator 1116 is separated from the auto-injector 1115 in the second auto-injector arrangement 1110 state. In one arrangement the auto-injector 1115 is removed from the receptacle in the second auto-injector arrangement 1110 state. In one arrangement the auto-injector 1115 further comprises a compressed gas source that when opened provides gas pressure within the injector body 1111 to expel the beneficial agent, and wherein the compressed gas source is incapable of opening in the first auto-injector arrangement 1110 state, and the compressed gas source is capable of being opened in the second auto-injector arrangement 1110 state. The injector body 1111 comprises an activation member 1117 extending therefrom that, when moved toward the injector body 1111, activates the auto-injector 1115 to expel the beneficial agent, and wherein the actuator 1116 impedes the activation member 1117 from moving toward the injector body 1111 in the first auto-injector arrangement 1110 state. The activation member comprises an injection end 1119 from where the beneficial agent is expelled.

According to one aspect of the auto-injector arrangement 1110, the auto-injector 1115, comprises: (a) an injector housing 1111 having an injection end 1114; (b) an administration assembly 1121 disposed within the injector housing, the administration assembly 1121 having a delivery end 1119 proximate to the injection end 1114 through which a beneficial agent housed within the administration assembly 1121 is capable of being expelled; and (c) an actuator 1116 moveably connected to the administration assembly 1121, wherein: when in a first auto-injector 1115 state, the actuator 1116 is coupled to the administration assembly 1121 1121 such that the delivery end 1119 is rendered incapable of being applied to a subject and the administration assembly 1121 is rendered incapable of expelling the beneficial agent; and when in a second auto-injector 1115 state, corresponding to the actuator 1116 having been manipulated from the first auto-injector 1115 state, the administration assembly 1121 is rendered capable of expelling the beneficial agent, the auto-injector 1115 thereafter movable into a third auto-injector 1115 state in which the actuator 1116 is separated from the auto-injection 1115. Manipulating the actuator 1116 from the first auto-injector 1115 state to the second auto-injector 1115 state comprises moving the actuator 1116 relative to the injector housing. In one arrangement the administration assembly 1121 comprises a first compartment for storing at least a first constituent of the beneficial agent, and at least a second compartment for storing at least a second constituent of the beneficial agent separate from the first constituent; and wherein at the second auto-injector 1115 state, the first compartment and the at least second compartment are merged.

FIGS. 12a and 12b illustrate an auto-injector arrangement 1220 activatable to administer a beneficial agent to a subject comprising an auto-injector 1210 comprising: (a) an auto-injector body 1221, comprising an injection end 1226, and (b) an actuator 1222, wherein, at the first auto-injector state (peruse configuration) shown in FIG. 12a, is mounted on the injection end 1226. The auto-injector arrangement 1220 is moveable from a first auto injector state (pre-use configuration) where activation is disabled, to a second auto-injector state (an armed configuration) where activation is enabled. The auto-injector body 1221 comprises helical ramps 1225, and the actuator 1222 comprises reciprocal helical ramps 1223 such that at the first auto-injector 1210 state, when the cap is rotated counter clock wise the auto-injector 1210 is moved from the first auto-injector 1210 state to the second auto-injector 1210 state, thereafter the auto-injector 1210 is separated from the actuator 1222 as shown in FIG. 12*b*. The actuator 1222 can be joined to an anchoring body for instance by threading a strap, or a band (i.e. anchoring link) in through hole 1229 such that rotating the auto-injector 1210 relative to the anchoring body will move the auto-injector 1210 from the first auto-injector state to the second auto-injector state. The anchoring body may be a garment, a package, a bag a pouch, a kit, a container, an enclosure, a combination thereof, or other objects that the auto-injector may need to connect to. According to one aspect of the auto-injector arrangement 1220, the auto-injector 1210, comprises: (a) an injector housing 1221 having an injection end 1211; (b) an administration assembly 1212 disposed within the injector housing 1221, the administration assembly 1212 having a delivery end 1213 proximate to the injection end 1211 through which a beneficial agent housed within the administration assembly 1212 is capable of being expelled; and (c) an actuator 1222 moveably connected to the administration assembly 1212, wherein: when in a first auto-injector 1210 state, the actuator 1222 is coupled to the administration assembly 1212 such that the delivery end 1119 is rendered incapable of being applied to a subject and the administration assembly 1212 is rendered incapable of expelling the beneficial agent; and when in a second auto-injector 1210 state, corresponding to the actuator 1116 having been manipulated from the first auto-injector 1210 state, the administration assembly 1212 is rendered capable of expelling the beneficial agent, the auto-injector 1210 thereafter movable into a third auto-injector 1210 state in which the actuator 1222 is separated from the auto-injection 1210. Manipulating the actuator 1222 from the first auto-injector 1210 state to the second auto-injector 1210 state comprises moving the actuator 1222 relative to the injector housing 1221. In one arrangement the administration assembly 1212 comprises a first compartment for storing at least a first constituent of the beneficial agent, and at least a second compartment for storing at least a second constituent of the beneficial agent separate from the first constituent; and wherein at the second auto-injector 1210 state, the first compartment and the at least second compartment are merged.

Figures 13A, 13B:
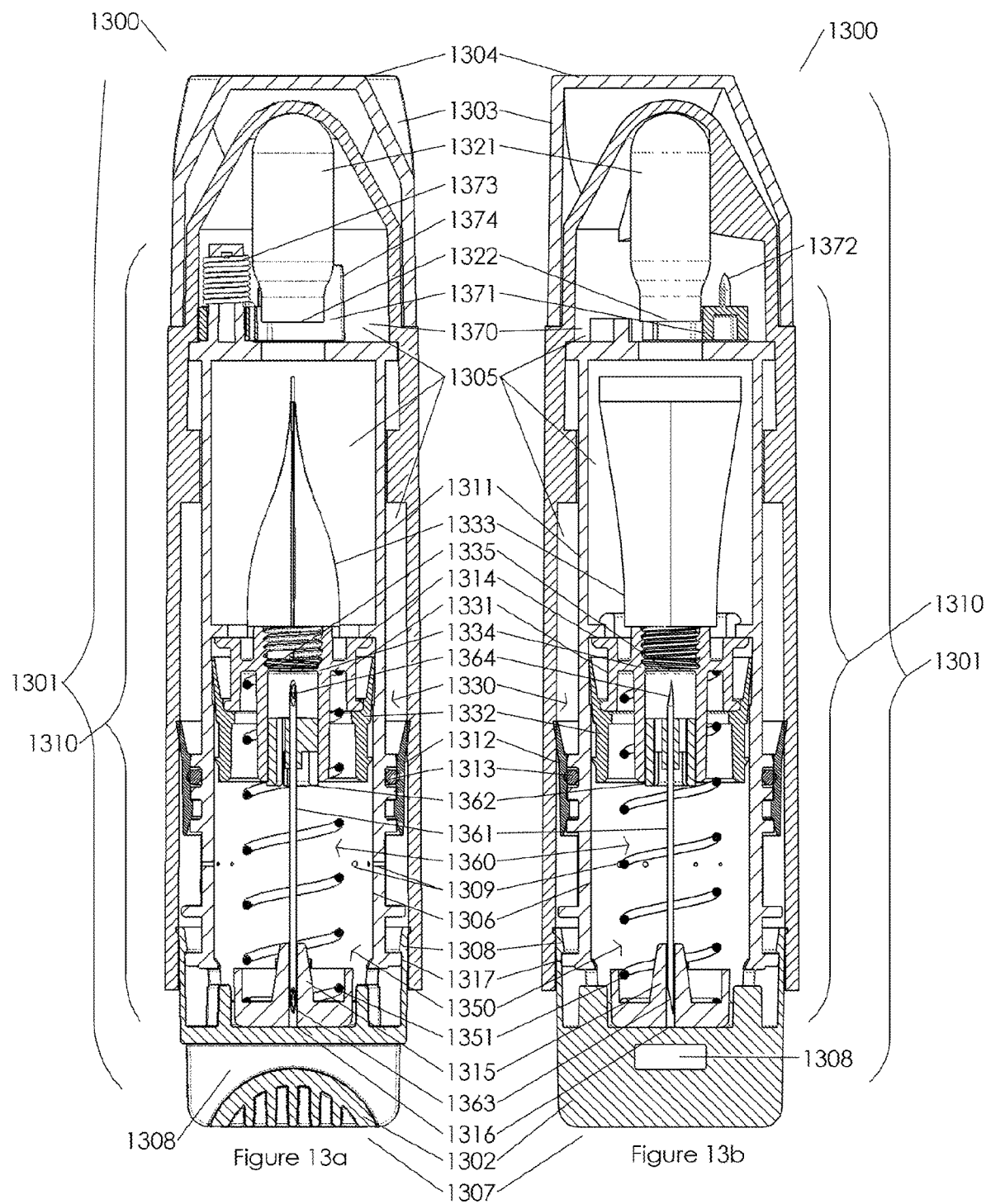
FIGS. 13a-13n illustrate an auto-injector arrangement and detailed operation sequence steps according to various embodiments described herein.
Figures 13E, 13F:
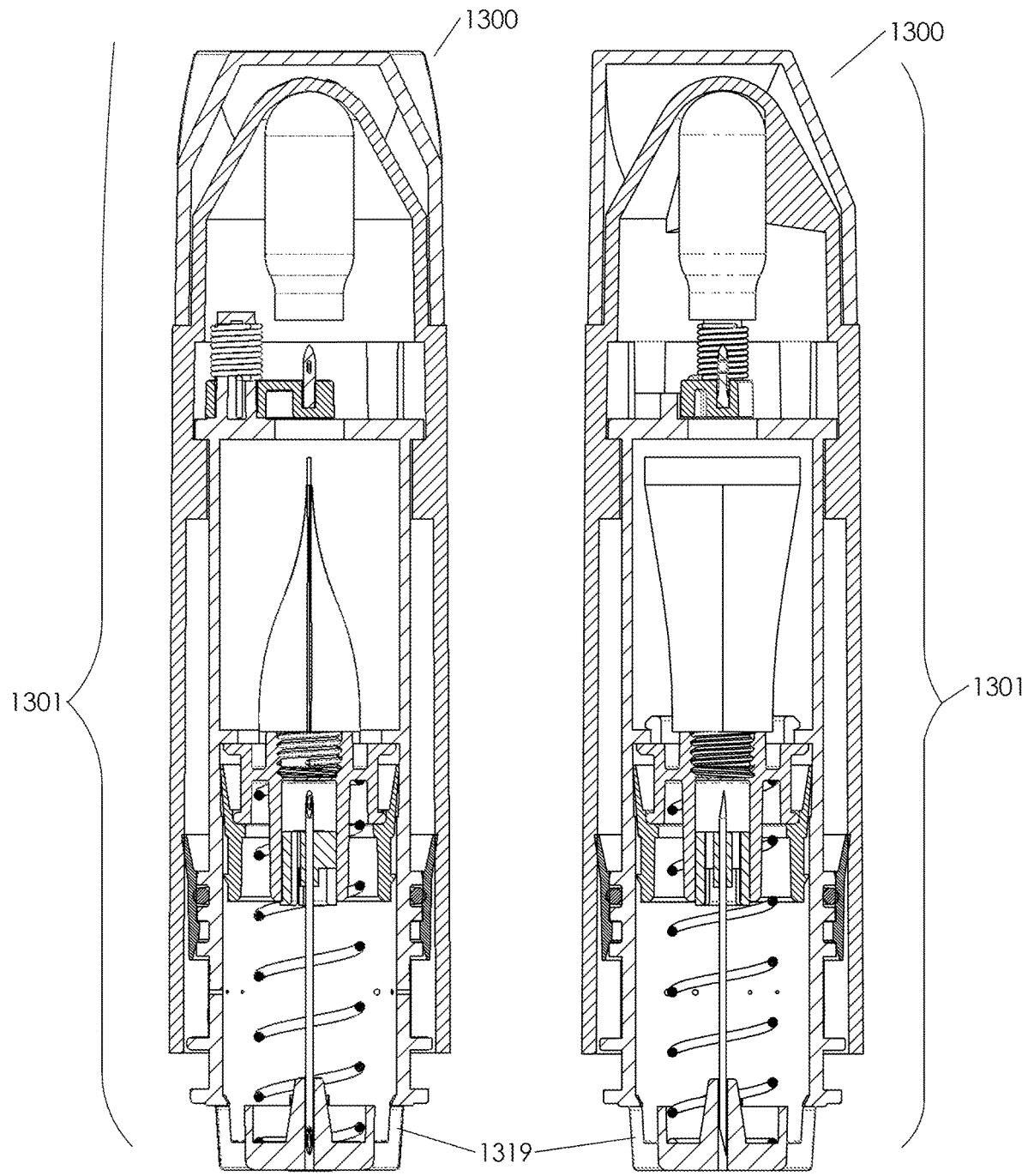
Figures 13G, 13H:
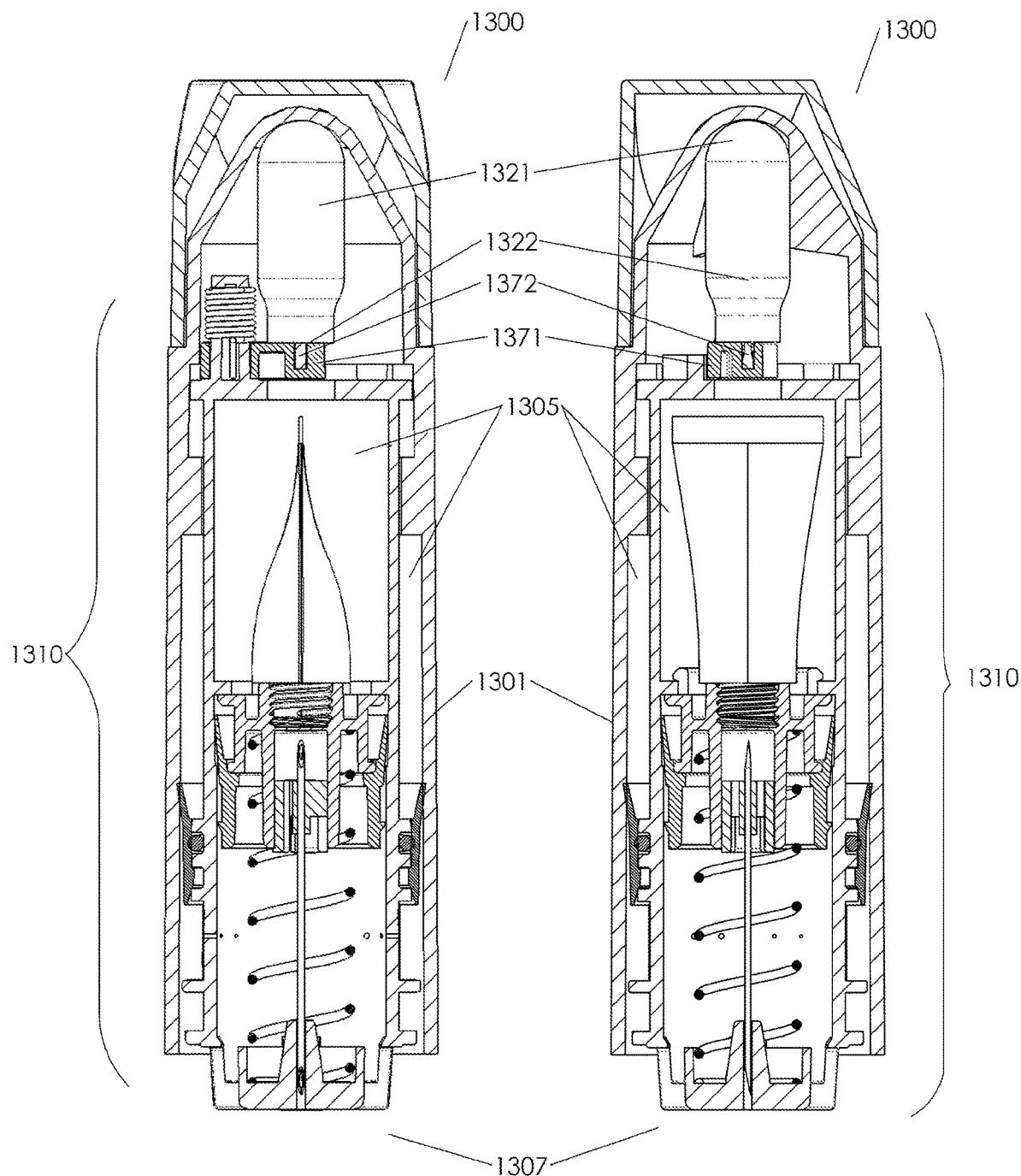
Figures 13I, 13J:
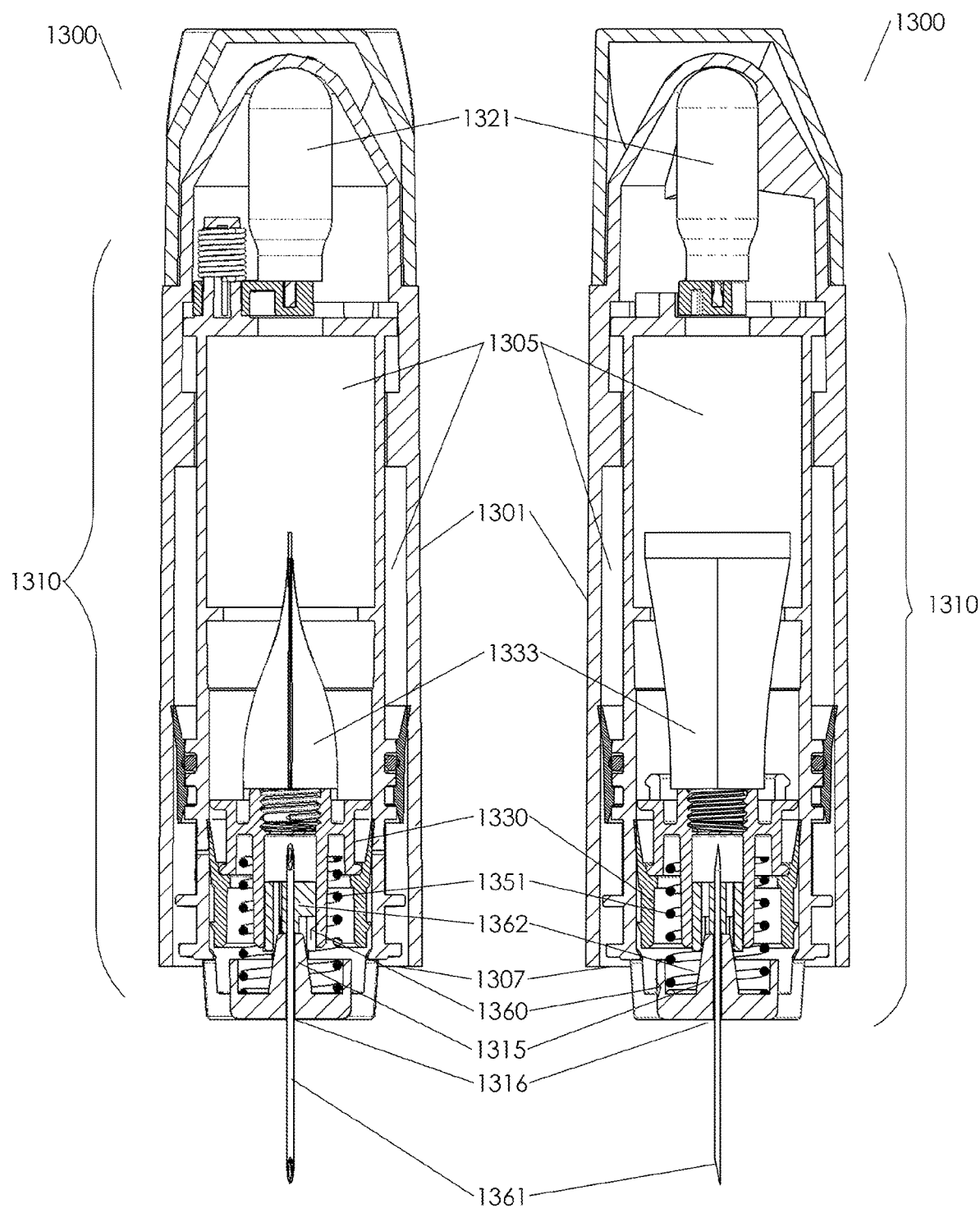
Figures 13K, 13L:
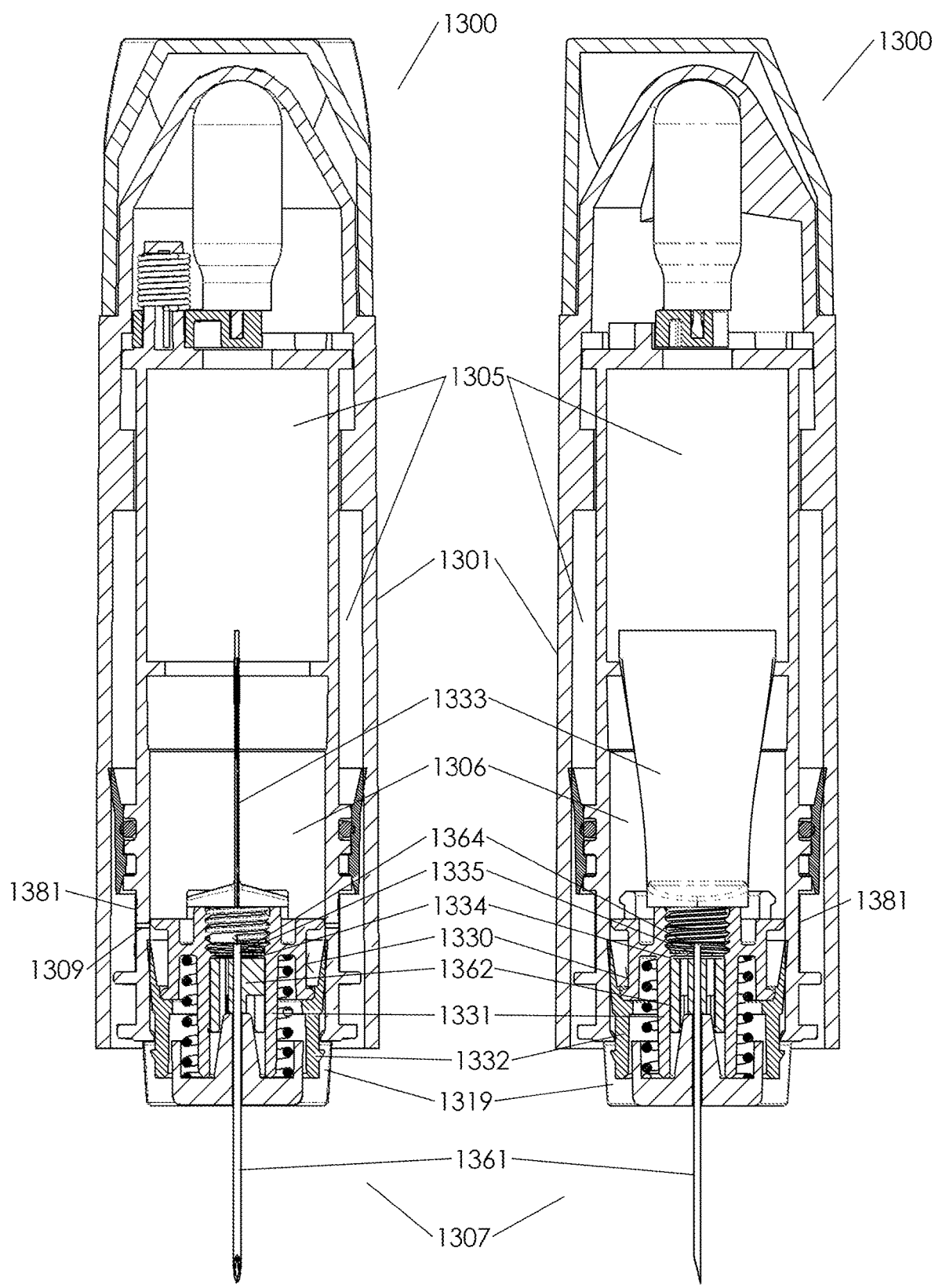
Figures 13M, 13N:
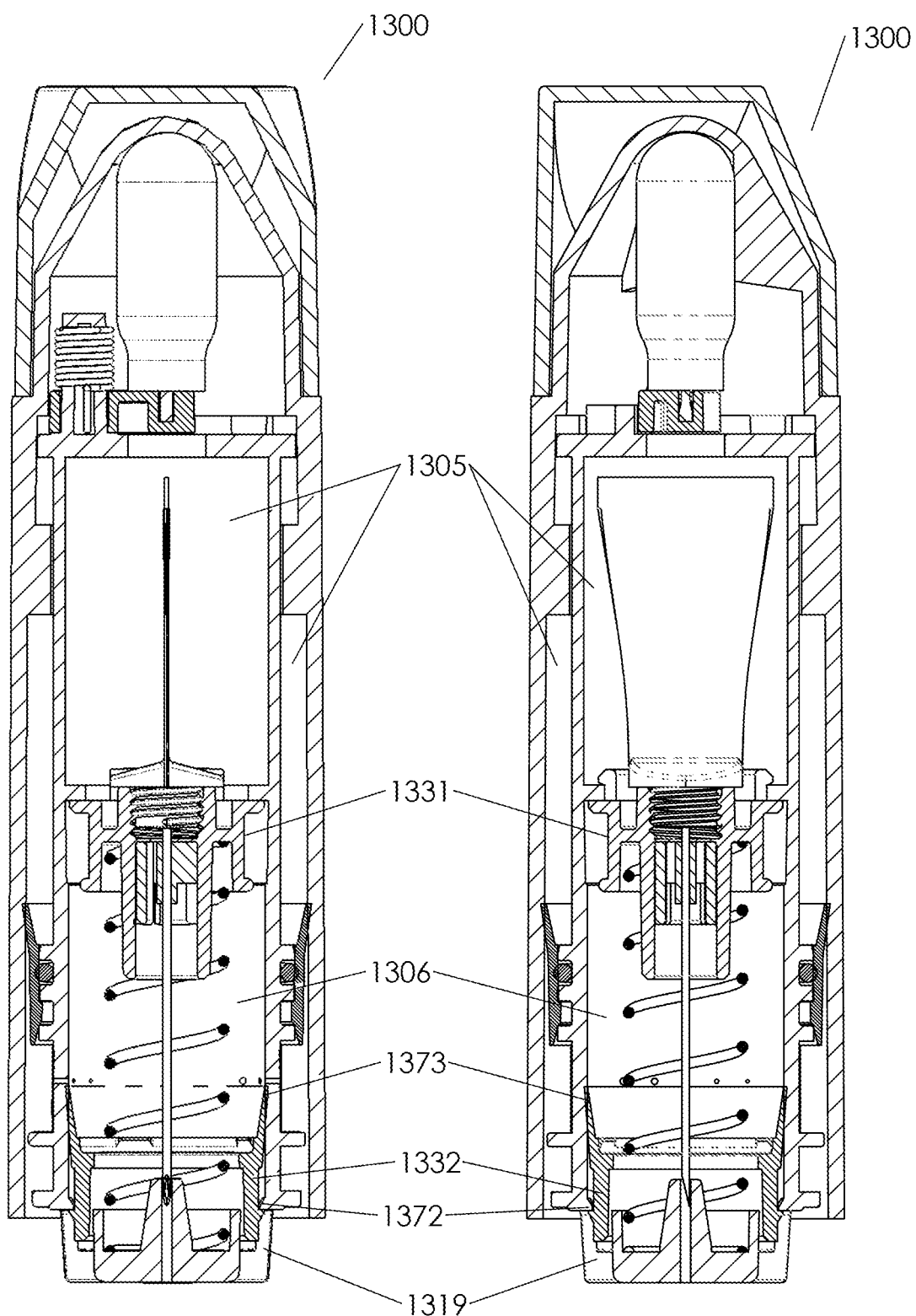

FIGS. 13*a* to 13*n* illustrate an auto-injector 1300 of the present disclosure in several operation sequence configurations. The auto-injector 1300 is activatable to administer a beneficial agent to a subject. The auto-injector 1310, comprises: (a) an injector housing 1301 (also referred to as auto-injector body 1301) having an injection end 1307; (b) an administration assembly 1310 disposed within the injector housing 1301, the administration assembly 1310 having a delivery end 1316 proximate to the injection end 1307 through which a beneficial agent housed within the administration assembly 1310 is capable of being expelled; and (c) an actuator 1302 (also referred to as cap 1302 or sterile cap 1302) moveably connected to the administration assembly 1310, wherein: when in a first auto-injector 1300 state, the actuator 1302 is coupled to the administration assembly 1310 such that the delivery end 1316 is rendered incapable of being applied to a subject and the administration assembly 1310 is rendered incapable of expelling the beneficial agent; and when in a second auto-injector 1300 state, corresponding to the actuator 1302 having been manipulated from the first auto-injector 1300 state, the administration assembly 1310 is rendered capable of expelling the beneficial agent, the auto-injector 1300 thereafter movable into a third auto-injector 1300 state in which the actuator 1302 is separated from the auto-injection 1300. Manipulating the actuator 1302 from the first auto-injector 1300 state to the second auto-injector 1300 state comprises moving the actuator 1302 relative to the injector housing 1301. In one arrangement the administration assembly 1310 comprises a first compartment for storing at least a first constituent of the beneficial agent, and at least a second compartment for storing at least a second constituent of the beneficial agent separate from the first constituent; and wherein at the second auto-injector 1300 state, the first compartment and the at least second compartment are merged.

FIGS. 13*a* and 13*b* illustrate longitudinal cross-sections of the auto-injector 1300 in a first auto-injector state (also referred to as the pre-use configuration). The auto-injector 1300 comprises an injector housing 1301 (also referred to as the auto-injector housing 1301 or the auto-injector body 1301) comprising an injection end 1307, aseptically protected by a sterile cap 1302, and an ornamental end piece 1303 joined to the distal end 1304 opposite to the injection end 1307. An administration assembly 1310 is axially moveable in the auto-injector body 1301 between a pre-use position, an armed position, and an activated position, corresponding to the first auto-injector state, the second auto-injector state, and the third auto-injector state respectively, as will be described hereunder. The administration assembly 1310 comprises a carriage 1311, a piston assembly 1330, a needle assembly 1360 and a beneficial agent package 1333. The administration assembly 1310 is air tight sealed against the auto-injector body via an O-ring seal 1313 and a wiper seal 1312. The wiper seal provides for a lower friction force as the administration assembly 1310 moves relative to the body 1301, and avoid sticking that sometimes occur when an O-ring is compressed against a sealing surface for an elongated time. A piston assembly 1330 is moveably disposed in the carriage 1311 and divides the internal volume of the auto-injector body 1310 into a pressure chamber 1305 and a sterile needle housing 1306. The piston assembly 1330 comprises a piston core 1331 and a piston wiper seal 1332 moveably joined in a fluid tight fashion. The piston wiper seal 1332 is moveably sealed in a fluid tight fashion with the needle housing walls 1306. A beneficial agent package 1333 in a form of a tube is disposed in the pressure chamber 1305 and is joined to the distal end of the piston core 1331, such that the spout of the tube is confronting a membrane 1334. The beneficial agent package 1333 comprises a compartment for storing at least one constituent of a beneficial agent, and a connector for joining the package 1333 to the piston core 1331. In one arrangement the package 1333 comprises a membrane 1335 for aseptically sealing the beneficial agent. The piston core 1331 is axially biased by a biasing mechanism 1350 comprising a spring 1351, to seat against stopper 1314—an inner circumferential ridge protruding from the carriage 1311. A needle assembly 1360 is disposed in the needle housing 1306 and is moveably joined to the proximal end of the piston core 1331. The needle assembly 1360 comprises a hypodermic needle 1361, having a proximal hypodermic bevel tip 1363, and a distal sharp tip 1364 configured to pierce into the beneficial agent package 1333; and a needle hub 1362. The needle hub 1362 is moveably disposed in a bore in the piston core 1331 in such a manner that substantial force is required to axially move the needle assembly 1360 relative to the piston core 1331. The force required to move the needle assembly 1360 relative to the piston core 1331 can be calibrated by several means including interference features, and friction. The proximal needle tip 1363 is received at the needle abutment 1315, confronting an opening in the delivery end 1316 in the administration assembly 1310. At this pre-use configuration the needle is concealed in the auto-injector body and is maintained sterile in the aseptically sealed needle housing 1306 by the aseptic cap 1302. The aseptic cap inner circumferential ridge 1308 seals against the cap detent ridge 1317 of the carriage 1311. The edge of the cap 1302 is confined in the auto-injector body, preventing the cap circumferential ridge 1308 from expanding and dislodging from the cap detent ridge 1317 of the carriage 1311. A compressed gas source in a form of metal cartridge 1321 is supported at the distal end of the auto-injector body 1301 in the pressure chamber 1305, and comprises a rupturable membrane, 1322 oriented toward the injection end 1307. An arming mechanism 1370 is moveably joined at the distal end of the carriage 1311. The arming mechanism 1370 comprises a piercing arm 1371 and a piercing element 1372 biased by torsion spring 1373 from a pre-use position, where the piercing element is not aligned with the cartridge membrane 1322 (as is clearly illustrated in FIG. 13*b* and later in FIG. 14*a*), to the armed position, which is illustrated in subsequent Figures. The piercing arm protrusion 1374 leans against the cartridge 1321 and prevent the piercing element 1371 from aligning with the cartridge membrane 1322. This arrangement of the arming mechanism is advantageous for its inherent safety as the piercing element 1372 cannot pierce the cartridge 1321 regardless of the force applied to the auto-injector body. Actuator 1302 comprises a through pass 1318 for hooking the auto-injector body 1301 to an anchoring link such as a lanyard, a chain, a ring, a strap or other form of attachments known in the art. In one arrangement the actuator 1302 is configured to connect to a receptacle wherein at least a portion of the auto-injector body 1301 is accommodated for storage or carrying. Forms of receptacles for auto-injector 1300 can be, but not limited to, a holster, a bracket, a cradle, a closure, a package, a bag, a pocket, a purse, a tube and a combination of the above.

In one arrangement the compressed gas source is at least partially external to the auto-injector body. In one such example the gas is supplied by a hose to the pressure chamber 1305. A valve, or a pierceable membrane can be accommodated in the auto-injector body 1301 to control the introduction of pressure to the pressure chamber 1305.

Figures 14A, 14B, 14C, 14D:
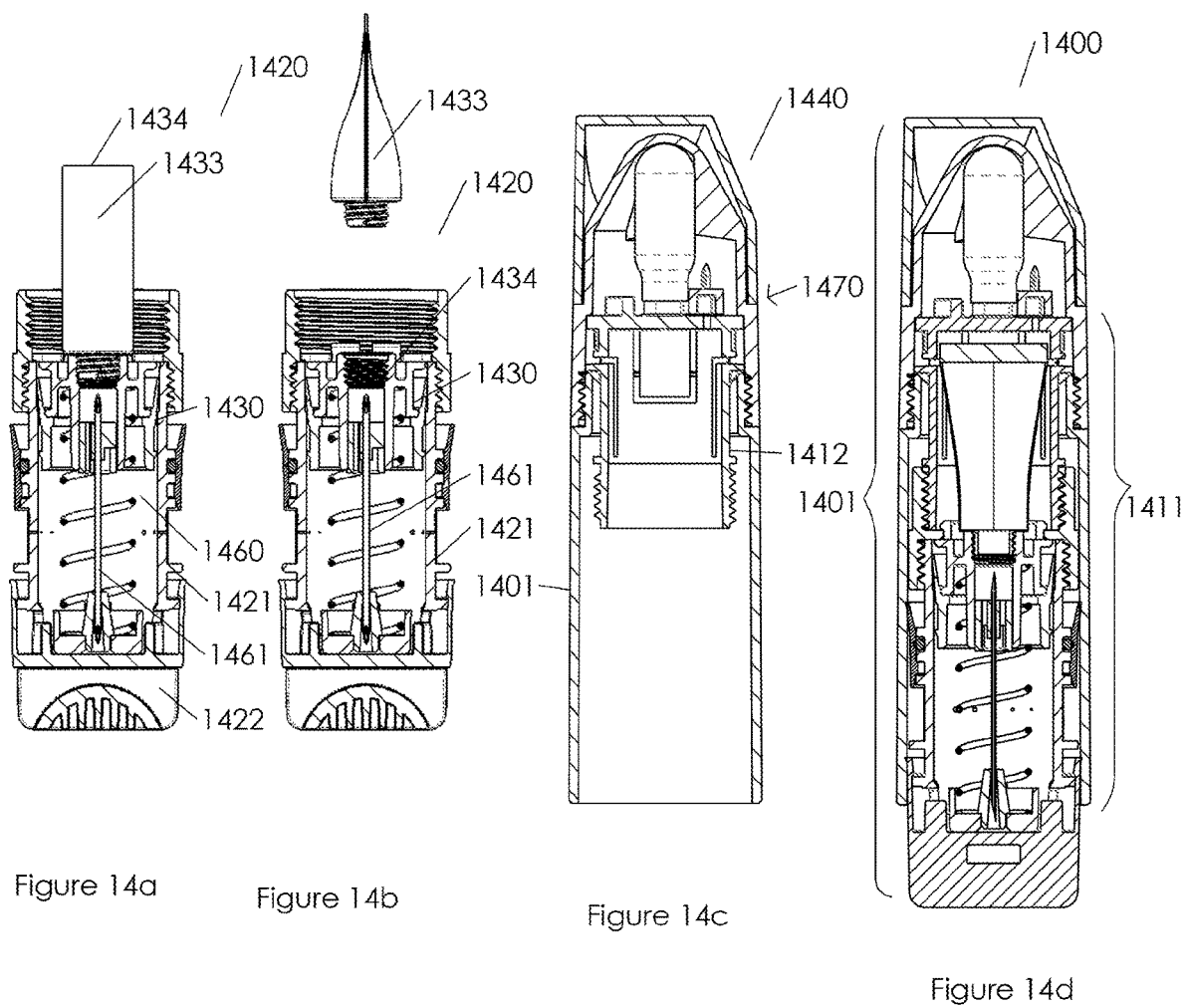
FIG. 14a-14f illustrate two manufacturing process options of an auto-injector according to various embodiments described herein.

The carriage can be formed from an assembly of parts that are joined by threads, screws, welding, gluing or other means known in the art such as in the arrangement illustrated in FIG. 14*c*.

Figure 15A:
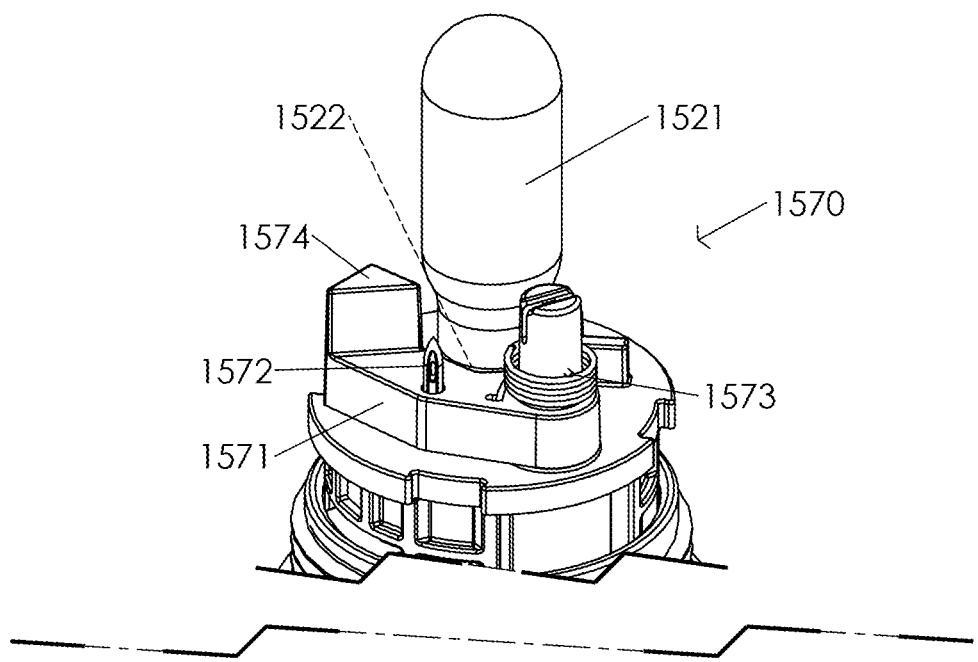
FIGS. 15a and 15b illustrate an arrangement of an arming mechanism of an auto-injector according to various embodiments described herein.
Figure 15B:
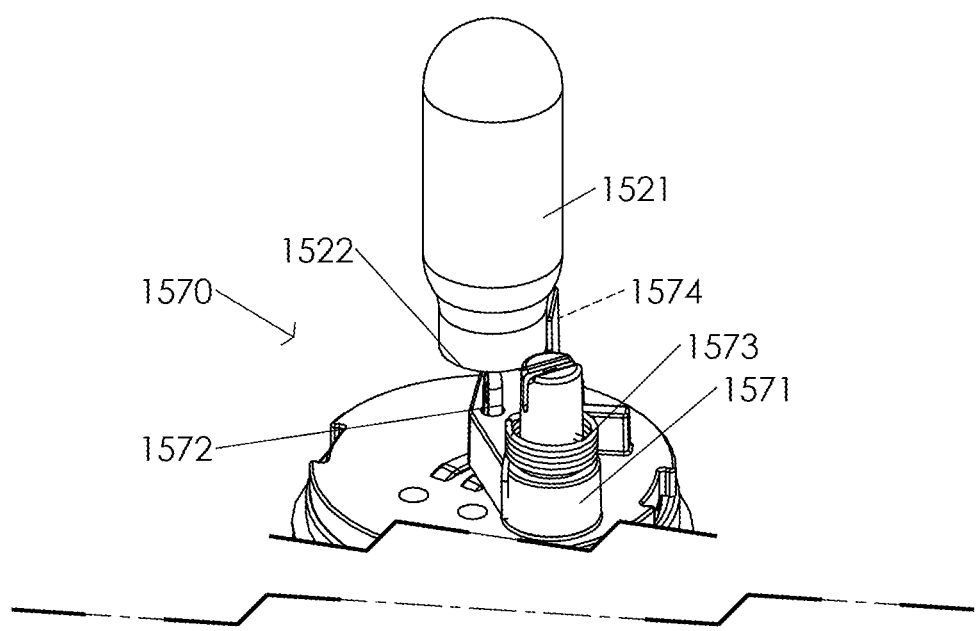

FIGS. 13*c* and 13*d* illustrate cross section views of the auto-injector 1300 in the second auto-injector state (also referred to as the armed configuration). The administration assembly 1310 is axially moved relative to the auto-injector body 1301 toward the injection end 1307, from its pre-use position to the armed position, at which point the piercing arm protrusion 1374 (not shown) disengages from the side of the gas cartridge 1321, allowing the torsion spring 1373 to move the piercing arm 1371 to the armed position where the piercing element 1372 is in a confronting position with the cartridge membrane 1322. A similar arrangement of the arming mechanism is illustrated in FIG. 15*a* and FIG. 15*b* and can provide further clarity to the principle of operation of this arming mechanism. The cap 1302 edge is dislodged from behind the auto-injector body 1301 allowing it to radially expand and to be removed from the cap detent ridge 1317 of the carriage 1311. The administration assembly 1310 can be manipulated from the pre-use position to the armed position by pulling the cap 1302 away from the auto-injector body 1301. In some arrangements the cap 1302 is attached to an anchoring link or an anchoring body such that the movement from the pre-use configuration to the armed configuration can be accomplished by merely grasping the auto-injector body in the palm and single-handedly moving it relative to the anchoring link or the anchoring body.

FIGS. 13*e* and 13*f* illustrate cross section views of the auto-injector 1300 in the third auto-injector state when the cap 1302 is removed and the auto-injector 1300 is ready for injection. The use indication windows 1319 are exposed when the cap 1302 is removed. In some arrangements the cap 1302 is connected to an anchoring link or a receptacle and is removed by merely grasping the auto-injector body 1301 in the palm and moving it relative to the anchoring link or the receptacle. In one arrangement the auto-injector 1300 is moved from the first auto-injector state (pre-use configuration) illustrated in FIG. 13*a-b*, to the third auto-injector state (armed configuration with the cap 1302 removed) as shown in FIG. 13*e-f* in a single continuous action. Accordingly, in an arrangement where the cap 302 is connected to an anchoring link or an anchoring body, the auto-injector 1300 is moved from the first auto-injector state to the third auto-injector state where it is ready for injection by separating it from the anchoring link or the anchoring body, in a single hand operation, which is a unique feature of the present disclosure.

FIGS. 13*g* and 13*h* provide longitudinal cross-sections of the auto-injector 1300, showing a snapshot of the device as it is activated to expel the beneficial agent. The administration assembly 1310 is moved relative to the auto-injector body 1301 toward its distal end, causing the piercing element to pierce through the cartridge membrane 1322, thereby opening the pressure source 1321, allowing the compressed gas to fill the pressure chamber 1305. Several type of gas can be loaded in the cartridge 1321 in a gaseous or two-phase form including nitrogen, argon and carbon-dioxide. The administration assembly 1310 can be moved from the armed position to the activated position by grasping the auto-injector body 1301 in the palm in substantially the same hand grasped used to move the auto injector 1300 from the first auto-injector state to the second and third auto-injector state, and pressing the injection end 1307 against the subject's target injection site. In one arrangement the palm grasp of the auto-injector body 1301 for activating the auto-injector 1300 is substantially the same as the palm grasp used to move the auto-injector body from the pre-use configuration to the armed configuration, hence, combined with the arrangement described in the discussion of FIGS. 13*e-f*, in this arrangement the auto-injector 1300 can be operated from a pre-use configuration to an activation in a single hand operation without changing the palm grasp, which is a unique feature of the present disclosure that simplify the device 1300 operation and reduces the room for user errors.

FIGS. 13*i* and 13*j* provide longitudinal cross-sections of the auto-injector 1300, showing a snapshot of the device in the activation position shortly after the cartridge 1321 is pierced and the pressure chamber 1305 is pressurized. When the pressure at the pressure chamber 1305 surpasses a first threshold value, it exerts a force on the piston assembly 1330 that overcomes the preloaded biasing spring 1351 force, causing the piston assembly 1330 to move, together with the package 1333 and the needle assembly 1360, toward the injection end 1307, while extending the needle 1361 through the opening in the delivery end 1316. The needle 1306 reaches its extended position when the needle hub 1362 is stopped by the needle abutment 1315. The package 1333 is still not in communication with the needle, preventing injection of the beneficial agent before the needle 1361 has reached its fully extended position. As the pressure in the pressure chamber 1305 continues to force the piston assembly toward the injection end 1307, a relative movement between the needle assembly 1360 and the piston assembly 1303 is initiated as illustrated in FIGS. 13*k*-l.

FIGS. 13*k* and 13*l* provide longitudinal cross-sections of the auto-injector 1300 during injection. The pressure in the pressure chamber 1305 continued to move the piston assembly 1330 toward the injection end 1307. With the needle assembly 1360 now stationary, the piston assembly 1330 moves relative to the needle assembly 1360 causing the back end of the needle 1364 to pierce the piston core membrane 1334 and the tube membrane 1335, and establish fluid communication between the package 1333 and the needle 1361, allowing the beneficial agent to be administered. The pressure in the pressure chamber 1305 compresses the package 1333 to deliver the beneficial agent. As would be obvious to those skilled in the art, several packages are practically applicable for this auto-injector 1300 beside a tube, so long as they provide the adequate connection to the piston core 1331 and that their volume can be depleted by applying pressure to at least one of their walls. Such packages include, but are not limited to, metal tubes, laminated tubes, plastic tubes, molded tubes, tubes made from extruded material, blow molded packages, Blow-Fill-Seal packages, blister packages, pouch, sachet, bags, injection molded packages, and piston-barrel arrangements, and combination of the formers. In some arrangement of the auto-injector, one of the package membrane 1335 and piston core membrane 1334 is eliminated. The purpose of these membranes 1335, 1334 is to maintain the needle housing 1306 and the package 1333 aseptically sealed, however, as will be demonstrated in the description of FIG. 14, in certain manufacturing procedures of the auto-injector 1300 the piston core 1331 and the package 1333 are joined prior to filling of the beneficial agent, and prior to sterilization of the needle housing 1306, thus one membrane can provide the aseptic seal of the needle housing 1306 and the package 1333. In one arrangement the piercing element is other than the distal tip of the needle 1364. In one arrangement the needle 1361 terminates in the needle hub 1362 and the piercing element extends from the distal end of the needle hub 1362 either as a protruded extension of the needle hub 1362 or a separate part that is joined to the needle hub 1362 and extends from its distal end. When the piston assembly 1330 reaches the final activation position, the piston wiper is located under bleeding holes 1309 allowing the compressed gas to vent from the pressure chamber 1305. The pressure bleeding is used to control the dwelling time of the needle 1361 in the extended position, to allow enough time for the beneficial agent administration. This arrangement is particularly beneficial as the pressure bleeding cannot occur until the needle 1361 is fully extended, ensuring that: a) maximum pressure is available to force the needle insertion, and b) accurate timing of the needle dwelling in the extended position. As more clearly noticed in FIGS. 13*a-b*, bleeding holes 1309 of several sizes are embedded in the needle housing 1306 wall. These bleeding holes 1309 can be sealed, leaving the desired bleeding holes 1309 open, to achieve a desired bleeding rate, i.e. a desired dwell time. Other controllable bleeding passageway can be implemented to vent the pressure chamber including a valve, a labyrinth, etc. The bleeding holes 1309 are covered with a filter 1381 such as a Tyvek breathable laminate to prevent contamination of the needle housing 1305 prior to use of the device 1300. Piston wiper seal 1332 is now showing in the use indication windows 1319, indicating that the needle 1361 is fully extended and that the beneficial agent administration is taking place.

FIGS. 13*m* and 13*n* provide longitudinal cross-sections of the auto-injector 1300 after the needle 1361 has retracted. When the pressure in the pressure chamber drops under a second threshold pressure value, the spring 1351 moves the piston core 1331 away from the injection end 1307, separating from the piston wiper seal 1332 which is retained in its activated position due to a combination of friction with the needle housing 1306 wall and interference of the wiper seal lip 1383 with inward protrusions 1382. As soon as the piston core starts its back travel, the seal between the piston core 1331 and the piston wiper seal is breached, causing a sudden drop of pressure in the pressure chamber 1305 to the surrounding pressure. With no pressure in the pressure chamber 1305 and no seal friction force to counter, the spring 1351 force causes the piston core 1331, together with the needle assembly 1360, to abruptly retract to the pre-use position. This is particularly advantageous as: a) slow needle retraction can cause discomfort to the subject, and b) the abrupt needle retraction provides a tactile confirmation to the user/operator that injection is completed, and c) it reduces the chance of needle 1361 exposure after the device 1300 has been removed from the subject.

According to one aspect of the arrangement of FIGS. 13*a* to 13*n*, the auto-injector 1300 comprises an injector body 1301 housing a beneficial agent; and an actuator 1302 moveably connected to the auto-injector 1300, the actuator 1302 is adapted to be connected to an anchoring link which is adapted to be connected to an anchoring body, wherein: when in a first auto-injector 1300 state, corresponding to FIGS. 13*a-b*, the auto-injector is rendered incapable of expelling the beneficial agent; and when in a second auto-injector 1300 state, corresponding to FIGS. 13*c-d* where the auto-injector 1300 having being moved relative to the anchoring body from the first auto-injector 1300 state, the auto-injector 1300 is rendered capable of expelling the beneficial agent. Moving the auto-injector 1300 from the first auto-injector state to the second auto-injector state further comprises moving the actuator 1302 relative to the injector housing 1301. In one arrangement, in the second auto-injector 1300 state the actuator 1302 is separated from the auto-injector 1301. In one arrangement the anchoring link comprises at least one of a strap, a clip, a chain, a cable, a lanyard, a hook or a combination thereof. In one arrangement the injector body 1301 comprises a first compartment for storing at least a first constituent of the beneficial agent, and at least a second compartment for storing at least a second constituent of the beneficial agent separate from the first constituent; and when in a mixing auto-injector state, corresponding to the auto-injector having been moved relative to the anchoring body from the first auto-injector state, the first compartment and the at least second compartment are merged and the auto-injector 1300 is rendered incapable of expelling beneficial agent. In one arrangement transitioning the auto-injector 1300 from the first auto-injector state to the mixing auto-injector state comprises a first movement of the auto-injector 1300 relative to the anchoring body and transitioning the auto-injector 1300 from the mixing auto-injector state to the second auto-injector state comprises a second movement of the auto-injector 1300 relative to the anchoring body. In one arrangement the mixing auto-injector state and the second auto-injector state are the same. In one arrangement the actuator 1302 is separated from the auto-injector 1300 in the second auto-injector state. In one arrangement the auto-injector 1300 is removed from the anchoring body in the second auto-injector state. According to one aspect of the arrangement of FIGS. 13a-13n, the delivery end 1316 of the administration assembly 1310 acts as an activation member extending from the auto-injector body 1301 and, when moved toward the injector body 1301, the activation member activates the auto-injector 1300 to expel the beneficial agent, and wherein the actuator 1302 impedes the activation member from moving toward the injector body 1301 in the first auto-injector state.

According to one aspect of the arrangement of FIGS. 13a-13m, the auto-injector 1300 comprises: (a) an auto-injector body 1311 comprising an injection end 1307, (b) a needle assembly 1360 moveable from a pre-use position, where the needle assembly is concealed in the auto-injector body 1311, to a deployed position where the hypodermic tip of the needle 1361 extends from the auto-injector body 1307, (c) a biasing mechanism 1350 configured to bias the needle assembly 1360 to the pre-use position, (d) a pressure chamber 1305 (also referred to as pressure capsule 1305), and (e) a pressure release valve that, when opened, vents the pressure capsule; wherein when compressed gas pressure in the pressure chamber 1305 exceeds a first threshold pressure value, the needle assembly 1360 is moved to the deployed position, and when the pressure in the pressure chamber 1305 drops under a second threshold pressure value, the pressure release valve opens. The auto-injector 1300 further comprises a pressure bleeding passageway 1309 configured to gradually deplete the pressure in the pressure chamber 1305. The pressure release valve is configured to instantly deplete the pressure in the pressure chamber 1305. When the pressure release valve opens, at least a portion of the needle assembly abruptly retracts toward the auto-injector body 1311. The needle assembly 1360 is joined to a moveable piston 1330 that manipulates the needle 1361 from the pre-use position to the deployed position, and the pressure release valve is incorporated in the piston 1330. The biasing mechanism 1350 is configured to manipulate the release valve to open. The needle assembly 1360 is incorporated in the pressure release valve. The piston assembly 1330 comprises a first portion (i.e. piston core 1331) and a second portion (i.e. piston seal 1332), and the needle assembly 1360 is joined to the piston first portion 1331, and the biasing mechanism 1350 is a spring 1351 disposed between the injection end 1307 and the piston first portion 1331, such that the biasing mechanism 1350 manipulates the release valve to open by moving the piston first portion 1331 relative to the piston second portion 1332. The piston first portion 1331 retracts the needle 1361 toward the pre-use position when the pressure release valve is opened. The piston second portion 1332 provides a visual indication that the piston 1330 has moved to the deployed position. The bleeding passageway controls the timing of the opening of the pressure release valve.

According to one aspect of the arrangement of FIGS. 13a-13m, the auto-injector 1300 comprises: (a) an auto-injector body 1311 comprising an injection end 1307, (b) a compressed gas source 1321, (c) a needle assembly 1360, (d) a needle biasing mechanism 1350, (e) a calibrated pressure bleeding passageway 1309, and a pressure release valve; wherein the pressure profile produced by the combination of the pressure source 1321, the bleeding passageway 1309, and the release valve produces a sequence of: (f) deploying the needle 1361 from a pre-use position where it is substantially concealed in the auto-injector body 1311 to extend through the injection end 1307, (g) retain the needle 1361 in the deployed position for a defined time to deliver an injection, and (h) retract the needle 1361 toward the pre-use position.

According to one aspect of the arrangement of FIGS. 13a-13m, the auto-injector 1300 comprises: (a) a body 1311 comprising an injection end 1307, (b) a needle assembly 1360 moveable from a pre-use position to a deployed position, (c) an indicator 1332 moveable from a pre-use position to a deployed position; wherein when the needle assembly 1360 is moved from the pre-use position to the deployed position, the indicator 1332 is moved from the pre-use position to the deployed position, and when the needle assembly 1360 is removed from the deployed position the indicator 1332 remains in the deployed position. The needle assembly 1360 and the indicator 1332 are moved to the deployed position by a piston 1330. The piston assembly 1330 comprises at least a first portion 1331 and a second portion 1332, and the needle assembly 1360 is joined to the piston first portion 1331, and the piston second portion 1332 comprises the indicator. The auto-injector body 1311 comprises at least one indication window 1319, and the indicator 1332 shows in the indication window when in the deployed position. At its deployed position the indicator 1332 indicates that the needle 1361 has been deployed. In one arrangement at its deployed position the indicator 1332 indicates that the auto-injector 1300 has been used.

Figure 14E:
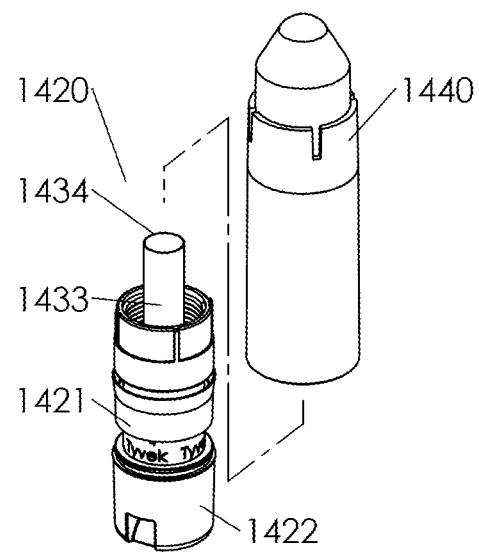
Figure 14F:
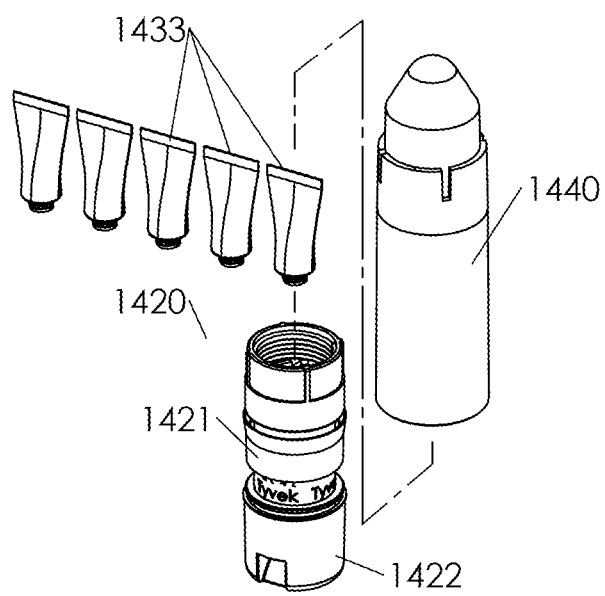

FIGS. 14a to 14f illustrate another arrangement of the auto-injector 1400 device of the present disclosure. The functionality of this arrangement is the same as that of the auto-injector 1300 illustrated in FIGS. 13a-n, but the construction of the administration assembly 1411, and the auto-injector body 1401 is configured to allow for a certain manufacturing process that will be described here under. FIGS. 14a and 14e illustrate a sterile assembly, comprising the needle housing 1421, the piston assembly 1430 to which the package 1433 is joined on its distal side, and the needle assembly 1460 is joined on its proximal side. The needle assembly 1460 is aseptically enclosed in the needle housing 1421. The sterile assembly 1420 can be provided to the beneficial agent filling site and filling equipment when it is pre sterilized and properly packaged to maintain sterility. The package 1433 is open at its distal side 1433 to allow filling of the beneficial agent, which after the distal end of the package 1434 is sealed. This filling step is preferably done in aseptic conditions, however once the package 1433 is sealed the sterile assembly 1420 can be moved out of the controlled filling environment as all the components that require sterility (i.e. the needle 1461, the beneficial agent, and the surfaces of the device that are to be in contact with the subject), are aseptically sealed. FIGS. 14b and 14f illustrate another filling process approach of the device 1400 where the package 1433 is filled prior to it being joined to the piston assembly 1430. The sterile assembly 1420 can be supplied sterile to the filing site in proper packaging. The piston core membrane 1434 provides an aseptic seal to the needle 1461 in the needle housing 1421 when the package 1433 is not joined to the sterile assembly 1420. FIG. 14c illustrate the pressure chamber assembly 1440, comprising the auto-injector body 1401, the distal portion of the administration assembly 1412, and arming mechanism 1470. In some arrangements the pressure chamber assembly 1440 doesn't need to be sterile, and can be joined with the already filled sterile assembly 1420 after the last has been out of the controlled environment. FIG. 14d illustrates the assembled device 1400 where the pressure chamber 1440 is joined with the sterile assembly 1420 by coupling the female thread at the distal end of the needle housing 1421 with the male thread of the distal portion of the administration assembly 1412 to form the complete administration assembly 1411.

FIG. 15a and FIG. 15b illustrate an arming mechanism, similar to the one illustrated in device 1300 of FIGS. 13a-n. A piercing arm 1571 comprises a cartridge piercing element 1572, and is biased toward the cartridge 1521 by the torsion spring 1573. FIG. 15a illustrates an arming mechanism in a safe state corresponding to the first auto-injector state (pre-use configuration) where protrusion 1574 leans against the cartridge 1521 side, preventing the piercing arm from moving toward the cartridge 1521. FIG. 15b illustrates the arming mechanism in an armed state corresponding to the second and third auto-injector states (armed configuration) in which the administration assembly 1521 has been axially moved relative to the cartridge 1521, such that the protrusion 1574 no longer leans against the cartridge 1521, allowing the piercing arm 1571 to move to the armed position where the cartridge piercing element 1522 is confronting the pierceable membrane 1522 of the cartridge 1521. In a subsequent activation step the cartridge 1521 is axially moved toward the piercing arm 1571 causing the piercing element 1522 to penetrate the cartridge membrane 1522.

The foregoing Figures and arrangements are provided by way of example and are not intended to limit the generality of this disclosure.

I claim:

1. An auto-injector arrangement, comprising:
an auto-injector comprising
an injector body housing a beneficial agent wherein the injector body comprises an activation member extending therefrom that, when moved toward the injector body, activates the auto-injector to expel the beneficial agent from an injector end, and wherein an actuator impedes the activation member from moving toward the injector body in a first auto-injector arrangement state; and
an administration assembly housed within the injector body and moveable relative to the injector body; and
the actuator moveably connected to the administration assembly, the actuator comprising an anchoring link adapted to be connected to an anchoring body, wherein;
when in the first auto-injector arrangement state, the auto-injector is rendered incapable of expelling the beneficial agent;
when in a second auto-injector arrangement state, the auto-injector is rendered capable of expelling the beneficial agent; and
when the actuator is moved relative to the injector body, the administration assembly is extended away from the injector body and the auto injector moves from the first auto-injector arrangement state to the second auto-injector arrangement state.

2. The auto-injector arrangement of claim 1 wherein at the second auto-injector arrangement state the actuator is separated from the administration assembly.

3. The auto-injector arrangement of claim 1 wherein the anchoring link comprises at least one of a strap, a clip, a chain, a cable, a lanyard, a hook or a combination thereof.

4. The auto-injector arrangement of claim 1 wherein the actuator comprises a cap.

5. The auto-injector arrangement of claim 4 wherein at the first auto-injector arrangement state, the cap isolates at least a portion of the auto-injector from the surrounding environment.

6. The auto-injector arrangement of claim 1 wherein the anchoring body comprises an auto injector receptacle inside of which, in the first auto-injector arrangement state, at least a portion of the auto-injector is accommodated, and wherein the receptacle comprises at least one of an enclosure, a package, a bag, a pouch, a pocket, a belt, a container, a holster, a cradle, a kit, a garment, or any combination thereof.

7. The auto-injector arrangement of claim 6 wherein the auto-injector is separated from the receptacle in the second auto-injector arrangement state.

8. The auto-injector arrangement of claim 1 wherein the relative movement comprises at least one of rotation, linear motion, or a combination thereof.

9. The auto-injector arrangement of claim 1, wherein:
the injector body comprises a first compartment for storing at least a first constituent of the beneficial agent, and at least a second compartment for storing at least a second constituent of the beneficial agent separate from the first constituent; and
when in a mixing auto-injector arrangement state, corresponding to the auto-injector having been moved relative to the anchoring body from the first auto-injector arrangement state, the first compartment and the at least second compartment are merged and the auto-injector is rendered incapable of expelling beneficial agent.

10. The auto-injector arrangement of claim 9 wherein transitioning the auto- injector arrangement from the first auto-injector arrangement state to the mixing auto-injector arrangement state comprises a first movement of the auto-injector relative to the anchoring body and transitioning the auto-injector arrangement from the mixing auto-injector arrangement to the second auto-injector arrangement state comprises a second movement of the auto-injector relative to the anchoring body.

11. The auto-injector arrangement of claim 9 wherein the mixing auto-injector arrangement state and the second auto-injector arrangement state are the same.

12. The auto-injector arrangement of claim 1 wherein the auto-injector further comprises a compressed gas source that when opened provides gas pressure within the injector body to expel the beneficial agent, and wherein the compressed gas source is incapable of opening in the first auto-injector arrangement state, and the compressed gas source is capable of being opened in the second auto-injector arrangement state.

* * * * *